(12) United States Patent
Zhou et al.

(10) Patent No.: US 11,427,575 B2
(45) Date of Patent: Aug. 30, 2022

(54) **ANTITUMOR COMPOUND FOR ACTIVATING *JWA* GENE AND DEGRADING HER2, PREPARATION METHOD THEREOF, AND APPLICATION THEREOF**

(71) Applicant: Jianwei Zhou, Nanjing (CN)

(72) Inventors: Jianwei Zhou, Nanjing (CN); Yanlin Ren, Nanjing (CN); Dongyin Chen, Nanjing (CN); Yefei Huang, Nanjing (CN); Aiping Li, Nanjing (CN)

(73) Assignee: SIMCERE PHARMACEUTICAL CO., LTD., Nanjing (CN)

( * ) Notice: Subject to any disclaimer, the term of this patent is extended or adjusted under 35 U.S.C. 154(b) by 183 days.

(21) Appl. No.: 16/992,089

(22) Filed: Aug. 12, 2020

(65) Prior Publication Data

US 2021/0047313 A1 Feb. 18, 2021

(30) Foreign Application Priority Data

Aug. 12, 2019 (CN) .......................... 201910739357.4

(51) Int. Cl.
*C07D 417/12* (2006.01)
*A61P 35/00* (2006.01)

(52) U.S. Cl.
CPC ............ *C07D 417/12* (2013.01); *A61P 35/00* (2018.01)

(58) Field of Classification Search
CPC .................................................... C07D 417/12
See application file for complete search history.

(56) References Cited

U.S. PATENT DOCUMENTS 4,369,323 A * 1/1983 Papenfuhs ........... C07D 277/82
548/156

* cited by examiner

*Primary Examiner* — Golam M Shameem
(74) *Attorney, Agent, or Firm* — Matthias Scholl P.C.; Matthias Scholl

(57) ABSTRACT

A compound as shown in formula I. $R^1$ is selected from the group consisting of —OH, —$CH_3$, —$CH_2CH_3$, —$OCH_3$, —$OCH_2CH_3$; $R^2$ is selected from the group consisting of —H, —OH, —$CH_3$, —$CH_2CH_3$, —$CH_2CH_2CH_3$, —$OCH_3$, —$OCH_2CH_2CH_3$; $R^3$ is selected from the group consisting of —F, —Cl, —Br, —I, —$CF_3$; $R^4$ is selected from the group consisting of —H, —F, —Cl, —Br, —I, —$CF_3$; and $R^5$ is selected from the group consisting of —H, —$CH_3$, —$CH_2CH_3$.

11 Claims, 19 Drawing Sheets

Specification includes a Sequence Listing.

GGTACCtgacttcctgtaactgagcactgaggctcagtgcatctctatttagcactcctcttactgtct
catatttaactagtgtttccactggattgcagaagttttgaaggcagagcaggattacattttctcct
ctttaaaaaaaaaagaaaagaaaagaaaaaaaacccacagtgctttcacagagcctcaaaagaactcg
aaatacttgctggcattgtactgaatattctcaaccttttcccctacccagatacatccacaacaata
aagttggagcaaggtagagaaaagttagtagatgtttataatgaaagcatagaaaacaaatcagattaa
agcactattaatagcaaacaagaatcgtgggctatcctattgctaataacaataatagtaacatataac
tgtgaacctttattatacactaagcatttcctatacattccttacttagcctcgtctatatggcagat
gttccattatccccactttacacatgaagacaccgaggctgggagagattaagtagtttctccaaagtc
acctgccagagaggaaggagctgcgactctaattttgctttctctgacttcacaccatcccatttttcc
agaatcaagaaaacatgagcactcaggaatattttcacattttaaactttattcaaaagcagcacata
agatatatcttagcactaattccatgcaatcaccaaatttcctaaacaacagtagtagtagtaatttc
ttagagtcgctgtaagctccttaactgtcttctgaattaataaggaaaattaaattatgttttctagac
tttgcattagtatatttcattactttccaagttttcaaaaattggtgatctgagtagagtgaattcacc
ttgtctaagccacttaggggcttagagactctgttatcttagaaatcttcaccttagaattctacctat
tacattatacaattaaacaaactacttttttttctcatgcattgtaccaatcagccccttaactgaaaaa
agatgaccctttggaagcttagaagagaattgacaacgaatacttcttttgccaggtctttgggctggga
tacaaaacatcacgttatctatgaatatattgtggtccctcagtgaaagctgtcaccaaatattgcaat
aaaactaagaaacttttgaagtggaatgcatatttctgcccagaaaatgctggatgcagaacaactag
ttcactgcagacaactgtttgctttaaaatgtaagcaacatgcccagctcaggactgaagtggccagag
tgcctactttatcagaatggcatagcagtccaacaatttagcctagagagaacagaggtggagaacaaa
gaagagaagtgaaaaaaacagaccagcccttctgttctacatgaccttctttcccgttttgccaatctg
atttcacacatagtgactcatggtgaaacagagaaaacatgggaattgcattcagatgtgtagaggtta
gtaagacttagttttcaaaagcagctcattctccattaacactgtagtcgccttccatttcatttcact
tagattggcatctgcacagctgccaaaattttttctctaagtcagagaacacactcctaggtaaaccttc
aaaaaaggtatttcgaaggaggcagcttctctgctgctagagaaggcattgccacctcccttcagacag
gggatttccgctagttgctttctgtcatttcgtctctattctgcactcagtcccttgttctgtctggag
gttcctgttttcctgtacccaaccaagagccaatgaagaagtaaagaggagcaaacacgcccgcccact
cccaatttcctttgctctgctgtctgccaaccgcaaagccgaccgagacggagccgctgtcaactctcc
aactcagctcagctgatcggttgccgccgccgccgccagattctggaggcgaagaacgcaaagctg
agaacGCTAGC

FIG. 1

| Analysis | Mock | vehicle | Groups 50mg/kg JAC1 | 100mg/kg JAC1 | TH |
|---|---|---|---|---|---|
| [ALT] | 29.33±2.52 | 30±4.24 | 32±2.65 | 23.75±2.22* | 29.75±4.5 |
| [AST] | 134.75±18.46 | 136±16.19 | 114.25±5.91 | 97±19.61* | 116.8±10.99 |
| [TP] | 39.03±3.44 | 42.24±5.07 | 45.48±8.91 | 42.16±5.21 | 41.6±3.69 |
| [ALB] | 26.23±0.81 | 27.35±3.48 | 33.95±2.26** | 29.95±1.19*** | 27.56±2.98 |
| [TBIL] | 0.47±0.15 | 0.43±0.15 | 0.55±0.29 | 0.58±0.1 | 0.62±0.11 |
| [ALP] | 212.25±41.05 | 235.75±68.86 | 233.25±55.06 | 186.8±33.89 | 179.5±67.78 |
| [GGT] | 4.67±1.15 | 4.01±0.01 | 6.03±1.48 | 4.22±1.41 | 3.46±0.65 |
| [GLU] | 8.6±2.27 | 8.53±3.87 | 7.48±2.05 | 11.05±4.03 | 9.9±2.82 |
| [BUN] | 8.93±2.4 | 10.1±1.42 | 9.9±2.34 | 12.2±1.83 | 12.13±2.03 |
| [CREA] | 19.33±1.15 | 19.5±1.29 | 20.75±2.75 | 20.75±0.96 | 20.75±2.99 |
| [UA] | 204.67±52.6 | 187.33±23.97 | 155.25±25.94 | 169.5±24.12 | 177.25±30.93 |
| [Ca] | 2.44±0.17 | 2.4±0.12 | 2.63±0.12 | 2.39±0.11 | 2.43±0.07 |
| [P] | 2.72±0.65 | 2.9±0.34 | 3.06±0.46 | 2.5±0.37 | 2.18±0.07 |
| [CHOL] | 2.58±0.17 | 2.48±0.19 | 3.18±0.04*** | 2.85±0.48 | 2.68±0.26 |
| [TG] | 1.25±0.37 | 1.17±0.32 | 0.79±0.21* | 0.63±0.12* | 1.14±0.49 |
| [HDLC] | 1.48±0.23 | 1.65±0.18 | 1.99±0.04** | 1.69±0.24 | 1.54±0.12 |
| [LDLC] | 0.46±0.04 | 0.48±0.04 | 0.48±0.08 | 0.44±0.07 | 0.51±0.07 |
| [LDH] | 1777.25±519.45 | 2010.25±308.79 | 1665.5±356.19 | 1344.83±490.88 | 1817.8±296.2 |
| [CKMB] | 437±127.14 | 513.25±26.99 | 361.2±54.12 | 296.17±48.52* | 408±100.13 |
| [SOD] | 51±18.19 | 70.5±14.62 | 110.6±22.84** | 92.17±15.3** | 77±18.67 |
| [CK] | 845.5±135 | 948±163.81 | 618.33±113.57* | 478.2±82.87*** | 703.6±172.3 |

FIG. 15

SEQUENCE LISTING

```
<160> NUMBER OF SEQ ID NOS: 1

<210> SEQ ID NO 1
<211> LENGTH: 2000
<212> TYPE: DNA
<213> ORGANISM: Artificial Sequence
<220> FEATURE:
<223> OTHER INFORMATION: Fully synthetic

<400> SEQUENCE: 1
tgacttcctg taactgagca ctgaggctca gtgcatctct atttagcact cctcttactg      60
tctcatattt aactagtgtt tccactggat tgcagaagtt ttgaaggcag agcaggatta     120 cattttctc ctctttaaaa aaaaaagaa aagaaaagaa aaaaaccca cagtgctttc       180 acagagcctc aaaagaactc gaaatacttg ctggcattgt actgaatatt ctcaaccttt     240
tccccctacc cagatacatc cacaacaata aagttggagc aaggtagaga aaagttagta     300
gatgtttata atgaaagcat agaaaacaaa tcagattaaa gcactattaa tagcaaacaa     360
gaatcgtggg ctatcctatt gctaataaca ataatagtaa catataactg tgaaccttta     420
ttatacacta agcatttcct atacattcct tcacttagcc tcgtctatat ggcagatgtt     480
ccattatccc cactttacac atgaagacac cgaggctggg agagattaag tagtttctcc     540
aaagtcacct gccagagagg aaggagctgc gactctaatt ttgctttctc tgacttcaca     600
ccatcccatt tttccagaat caagaaaaca tgagcactca ggaatatttt cacattttaa     660
actttattca aaaagcagca cataagatat atcttagcac taattccatg caatcaccaa     720
attttcctaa acaacagtag tagtagtaat ttcttagagt cgctgtaagc tccttaactg     780
tcttctgaat taataaggaa aattaaatta tgttttctag actttgcatt agtatatttc     840 attacttttcc aagttttcaa aaattggtga tctgagtaga gtgaattcac cttgtctaag     900
ccacttaggg gcttagagac tctgttatct tagaaatctt caccttagaa ttctacctat     960
tacattatac aattaaacaa actacttttt ttctcatgca ttgtaccaat cagcccctta    1020
actgaaaaaa gatgacccctt ggaagcttag aagagaattg acaacgaata cttcttttgc    1080
caggtctttg ggctgggata caaaacatca cgttatctat gaatatattg tggtccctca    1140
gtgaaagctg tcaccaaata ttgcaataaa actaagaaaa cttttgaagt ggaatgcata    1200
tttctgccca gaaaatgctg gatgcagaac aactagttca ctgcagacaa ctgtttgctt    1260
taaaatgtaa gcaacatgcc cagctcagga ctgaagtggc cagagtgcct actttatcag    1320
aatggcatag cagtccaaca atttagccta gagaaacag aggtggagaa caaagaagag    1380
aagtgaaaaa aacagaccag cccttctgtt ctacatgacc ttctttcccg ttttgccaat    1440
ctgatttcac acatagtgac tcatggtgaa acagagaaaa catgggaatt gcattcagat    1500
```

```
gtgtagaggt tagtaagact tagttttcaa aagcagctca ttctccatta acactgtagt   1560
cgccttccat ttcatttcac ttagattggc atctgcacag ctgccaaaat ttttctctaa   1620
gtcagagaac acactcctag gtaaaccttc aaaaaaggta tttcgaagga ggcagcttct   1680
ctgctgctag agaaggcatt gccacctccc ttcagacagg ggatttccgc tagttgcttt   1740
ctgtcatttc gtctctattc tgcactcagt cccttgttct gtctggaggt tcctgttttc   1800
ctgtacccaa ccaagagcca atgaagaagt aaagaggagc aaacacgccc gcccactccc   1860
aatttccttt gctctgctgt ctgccaaccg caaagccgac cgagacggag ccgctgtcaa   1920
ctctccaact cagctcagct gatcggttgc cgccgccgcc gccgccagat tctggaggcg   1980
aagaacgcaa agctgagaac                                               2000
```

ANTITUMOR COMPOUND FOR ACTIVATING *JWA* GENE AND DEGRADING HER2, PREPARATION METHOD THEREOF, AND APPLICATION THEREOF

CROSS-REFERENCE TO RELATED APPLICATIONS

Pursuant to 35 U.S.C. § 119 and the Paris Convention Treaty, this application claims foreign priority to Chinese Patent Application No. 201910739357.4 filed Aug. 12, 2019, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to the field of antitumor treatment, and more particularly, to an antitumor compound that activates JWA gene and degrades HER2, a preparation method thereof, and application thereof.

SUMMARY

The disclosure provides an antitumor compound capable of activating JWA gene and degrading human epidermal growth factor receptor 2 (HER2). Specifically, the antitumor compound can activate the JWA gene expression and further activate E3 ubiquitin ligase through biochemical cascades thereby degrading the HER2 protein, so that the antitumor compound exhibits a positive effect on inhibiting the growth of a malignancy promoted by the overexpression of HER2. In addition, the disclosure also provides a preparation method and applications for the antitumor compound.

Studies show that JWA protein can suppress the growth of the tumors. Most malignant tumor cells have a lower expression level of JWA protein than the normal surrounding tissue, while, conversely, overexpressing JWA protein leads to a decrease in the HER2 expression. Accordingly, a cell model is built to predict the expression level of a reporter gene introduced into a regulatory sequence of JWA gene promoter, and uses high-throughput screening to identify small molecules that will result in an activation of JWA gene expression. After being screened and identified from compound library, the small molecules undergo a verification of the potential antitumor effect on the malignant tumor cells in which HER2 protein is overexpressed.

An antitumor compound capable of activating JWA gene and degrading HER2 has the structure of Formula I:

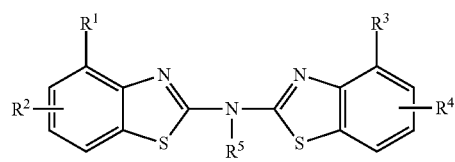

I $R^1$ is selected from the group consisting of —OH, —$CH_3$, —$CH_2CH_3$, —$OCH_3$, —$OCH_2CH_3$;

$R^2$ is selected from the group consisting of —H, —OH, —$CH_3$, —$CH_2CH_3$, —$CH_2CH_2CH_3$, —$OCH_3$, —$OCH_2CH_2CH_3$;

$R^3$ is selected from the group consisting of —F, —Cl, —Br, —I, —$CF_3$;

$R^4$ is selected from the group consisting of —H, —F, —Cl, —Br, —I, —$CF_3$; and $R^5$ is selected from the group consisting of —H, —$CH_3$, —$CH_2CH_3$.

The compound is a bisbenzothiazolamide compound.

Preferably, $R^1$ is —$OCH_3$; $R^2$ is —H or —$CH_3$; $R^3$ is —F, or —$CF_3$; $R^4$ is —H or —F; and $R^5$ is —H.

Preferably, the compound of Formula I is selected from the group consisting of: 4-fluoro-N-(4-methoxy benzene (d) thiazole-2-group) benzene (d) thiazole-2-amine; 4,7-difluoro-n-(4-methoxybenzo-thiazole-2-group) benzoylthiazole-2-amine; 4,6-difluoro-n-(4-methoxylbenzene (d) thiazole-2-group) benzene (d) thiazole-2-amine; 4-methoxy-N-(4-(trifluoromethyl) benzo (d) thiazole-2-group) benzo (d) thiazole-2-amine; N-(4-fluorobenzoyl (d) thiazole-2-group)-4,7-dimethoxy benzozoyl (d) thiazole-2-amine; N-(4-fluorobenzoyl (d) thiazole-2-group)-4,6-dimethoxy benzozoyl (d) thiazole-2-amine; 4,7-dimethoxyn-(4-(trifluoromethyl) benzene (d) thiazole-2-group) benzene (d) thiazole-2-amine; 4,6-dimethoxyn-(4-(trifluoromethyl) benzo (d) thiazole-2-group) benzo (d) thiazole-2-amine, with the following formulas, respectively:

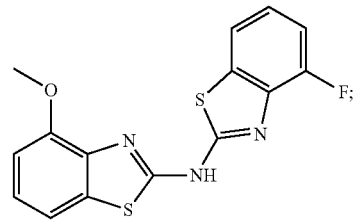

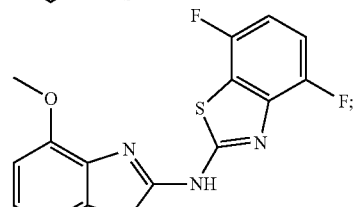

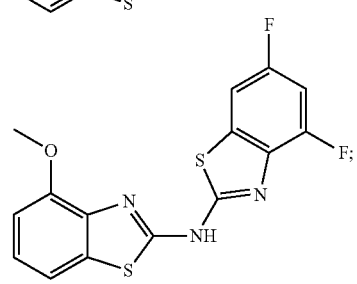

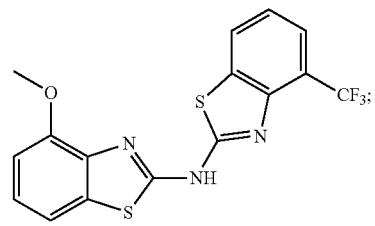

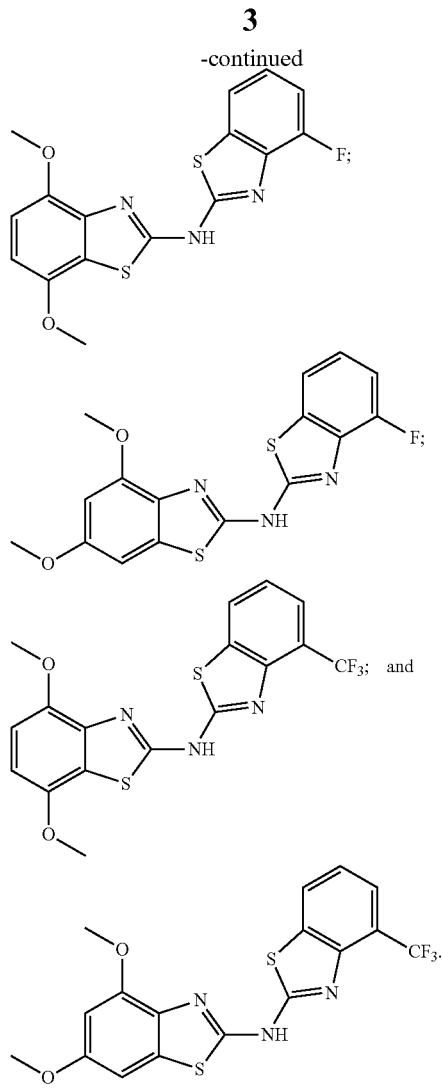

The results of the experiment indicated that the antitumor compounds lead to an effect on activation of cells and JWA gene expression in cells of tissues and organs in mice. The research indicates that each antitumor compound of the disclosure activates many biochemical cascades to specifically degrade HER2 protein overexpressed in tumor cells, such as activation of E3 ubiquitin ligase, and performs the function of inhibiting the abnormal proliferation and growth of tumor cells. A model of nude mice subcutaneously transplanted with human breast cancer cells overexpressing HER2 protein, is used to verify that the representatives of the antitumor compounds produce significant antitumor effect, and to some extent, provide protection to the specific functions of the major organs including heart, liver, and kidney of mice (more detailing in examples).

A method for preparing the antitumor compound, using the following flow chart:

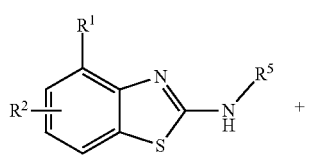

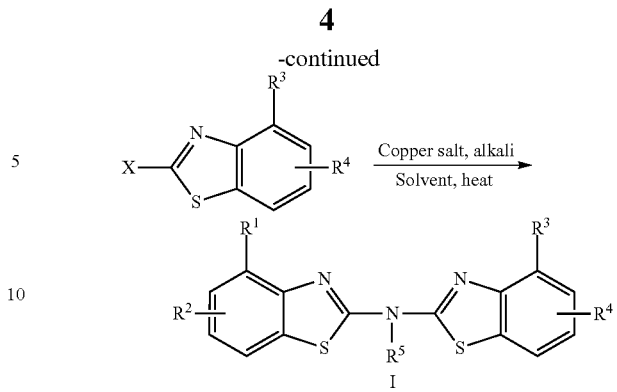

X is selected from the group consisting of Cl, Br, and I; the copper salt is selected from the group consisting of copper oxide, cuprous oxide, copper chloride, cuprous chloride, copper bromide, cuprous bromide and cuprous iodide; the alkali is selected from the group consisting of sodium hydroxide, potassium hydroxide, potassium carbonate, sodium carbonate, potassium tert-butoxide and sodium hydride; the solvent is selected from the group consisting of tetrahydrofuran, dimethyl sulfoxide and N,N-dimethylformamide; the heating temperature is 80-120° C. ($R^1$, $R^2$, $R^3$, $R^4$, and $R^5$ are the same as above, and not described herein again). Preferably, X is Cl; the copper salt is cuprous iodide; the alkali is potassium carbonate; the solvent is dimethyl sulfoxide; and the heating temperature is 100° C. The disclosure also provides a pharmaceutical salt of the antitumor compound.

Preferably, the pharmaceutical salt is a product formed by contacting the compound with an acid selected from the group consisting of hydrochloric acid, sulfuric acid, benzenesulfonic acid, p-toluenesulfonic acid, phosphoric acid, hydrobromic acid, maleic acid, fumaric acid and malic acid.

Also provided is a pharmaceutical composition comprising the antitumor compound or the pharmaceutical salt, or a combination thereof.

Further provided is a method of preparing a JWA gene activator or an antitumor drug, the method comprising applying the antitumor compound or a pharmaceutical composition comprising the antitumor compound.

The JWA gene activator or an antitumor drug is configured to activate JWA gene and repress HER2 protein of a tumor cell of breast cancer, gastric cancer, lung cancer, glioma, etc.; the antitumor drug inhibits the growth of the tumor by activating the JWA protein and degrading the HER2 protein.

The dosage form of the antitumor compound, the pharmaceutical salt, and the pharmaceutical composition are a tablet, powder, pill, capsule, suppository, granule, suspension, oral liquid, and injection; the oral tablet and the capsule comprise a conventional excipient such as fillers, lubricants, dispersants, diluents, and binders.

Compared with the prior art, the antitumor compound and the pharmaceutical salt thereof effectively increase the expression of JWA protein that activates many biochemical cascades to specifically degrade HER2 protein, such as activation of E3 ubiquitin ligase, further inhibiting the abnormal proliferation and growth of tumor cells.

The following advantages are associated with the antitumor compounds and the pharmaceutical salts thereof of the disclosure: The antitumor compounds and the pharmaceutical salts thereof can degrade HER2 protein overexpressed in the tumor cells, achieving a more encouraging antitumor effect than the current treatment methods for cancers with HER2 overexpression. The mechanism for the tumor suppression by the compounds of the disclosure is obviously different from that of various anti-HER2 antibodies or the inhibitors inhibiting the activity of the HER2 protein kinase that are being used internationally. With reference to the theory of molecular cell biology, a reason for the encouraging antitumor effect is that the compound of the disclosure reveals a vital function in HER2 protein degradation, which prevents the drug resistance caused by the adaptive allostery of HER2 protein interacting with the anti-HER2 antibodies or the inhibitors. The antitumor compounds and the pharmaceutical salts thereof of the disclosure also provides a significant antitumor effect at relatively low concentrations, while being virtually nontoxic to the normal tissue cells and providing protection for the vital organs including heart, liver, kidney, etc.

BRIEF DESCRIPTION OF THE DRAWINGS

FIG. 1 is a sequence containing a cDNA sequence (SEQ ID NO: 1) of JWA gene in accordance with Example 11 of the disclosure;

FIG. 15 is a table of serum biochemical indexes of JAC1 acting on major organs of nude mice subcutaneously transplanted with human breast cancer cells in accordance with Example 18 of the disclosure.

DETAILED DESCRIPTION

Figure 2:
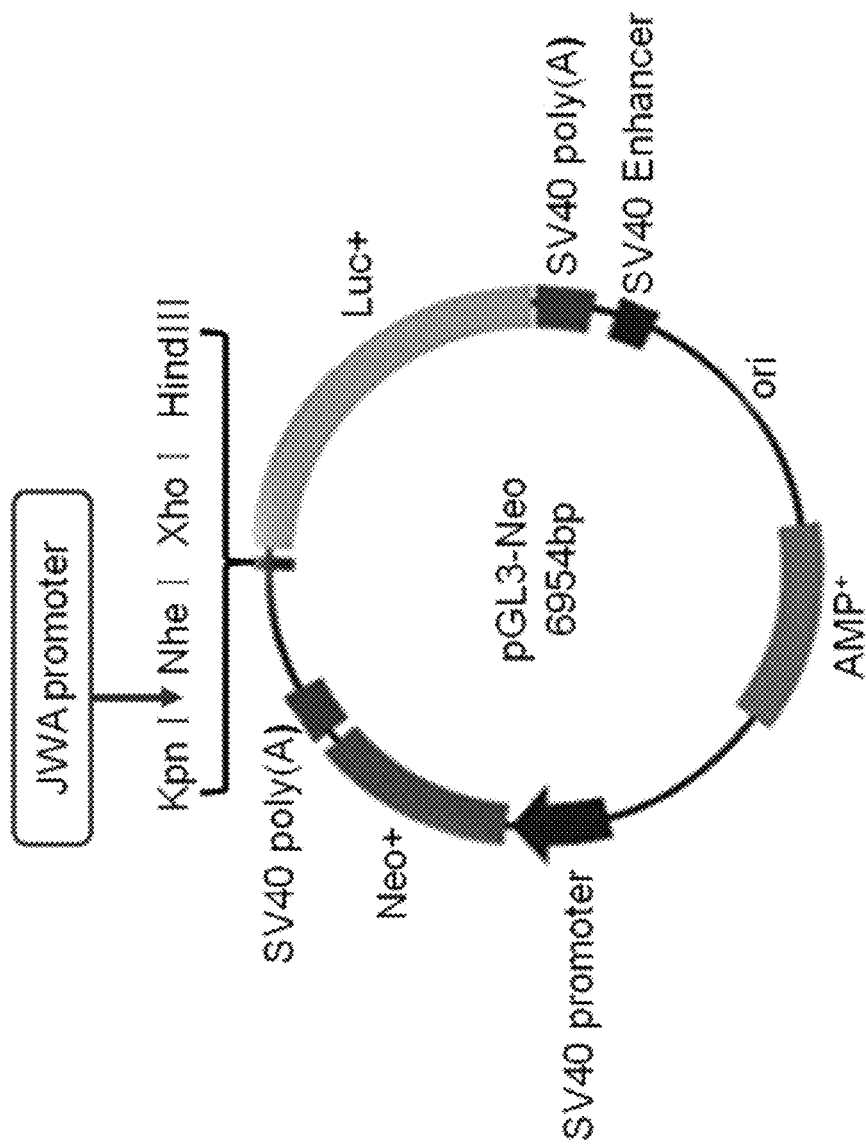
FIG. 2 is a molecular structure of a luciferase reporter containing the promoter sequence of JWA gene in accordance with Example 11 of the disclosure.

To further illustrate the disclosure, embodiments detailing an antitumor compound that activate JWA gene and degrade HER2, and preparation method and applications thereof are described below. It should be noted that the following embodiments are intended to describe and not to limit the disclosure.

Example 1

Preparation of 4-fluoro-N-(4-methoxy benzene (d) thiazole-2-group) benzene (d) thiazole-2-amine A magnet was added to a clean, dry 50 mL eggplant-shaped flask equipped with a spherical reflux condenser, followed by an addition of 2-chloro-4-fluorobenzo (d) thiazole (1 g, 5.3 mmol), 4-methoxybenzo (d) thiazole-2-amine (0.96 g, 5.3 mmol), cuprous iodide (0.31 g, 0.3 mmol), potassium carbonate (1.47 g, 10.6 mmol), dimethyl sulfoxide (20 mL). The temperature was raised to 100° C. and held for 6 h. After the reaction was complete, the mixture in the eggplant-shaped flask cooled down to room temperature, followed by an addition of distilled water (60 mL) and ethyl acetate (30 mL). The mixture was extracted 3 times, washed with distilled water and saturated brine, dried with anhydrous sodium sulfate, and filtered. The solvent was then moved by evaporation under reduced pressure to yield a first black solid. The first black solid was mixed with a silica gel powder, and purified by silica gel column chromatography with ($V_{PE}:V_{EA}$=5:1) as an eluent to yield a second black solid. After being slurried with ethyl acetate or methanol several times, the second black solid was transformed into a white solid compound 0.7 g (yield 39%).

$^1$H NMR (400 MHz, DMSO-$d_6$) δ 7.75 (d, J=5.8 Hz, 1H), 7.49 (d, J=7.9 Hz, 1H), 7.28-7.17 (m, 3H), 7.00 (d, J=8.0 Hz, 1H), 3.92 (s, 3H).

ESI-MS m/z: 332.1 ((M+H)$^+$).

Example 2

Preparation of 4,7-difluoro-n-(4-methoxybenzo-thiazole-2-group) benzoylthiazole-2-amine Example 2 was implemented with reference to the method of Example 1, and 2-chloro-4,7-difluorobenzo (d) thiazole was substituted for the 2-chloro-4-fluorobenzo (d) thiazole to yield an off-white solid 1.1 g (yield 57%).

$^1$H NMR (400 MHz, DMSO-$d_6$) δ 7.73 (d, J=5.4 Hz, 1H), 7.28-7.17 (m, 3H), 7.02 (d, J=8.0 Hz, 1H), 3.92 (s, 3H).

ESI-MS m/z: 350.1 ((M+H)$^+$).

Example 3

Preparation of 4,6-difluoro-n-(4-methoxylbenzene (d) thiazole-2-group) benzene (d) thiazole-2-amine Example 3 was implemented with reference to the method of Example 1, and 2-chloro-4,6-difluorobenzo (d) thiazole was substituted for the 2-chloro-4-fluorobenzo (d) thiazole to yield an off-white solid 0.8 g (yield 45%).

¹H NMR (400 MHz, DMSO-d₆) δ 7.65 (d, J=5.8 Hz, 1H), 7.35 (d, J=7.9 Hz, 1H), 7.28-7.17 (m, 2H), 7.03 (d, J=8.0 Hz, 1H), 3.92 (s, 3H).

ESI-MS m/z: 350.1 ((M+H)$^+$).

Example 4

Preparation of 4-methoxy-N-(4-(trifluoromethyl) benzo (d) thiazole-2-group) benzo (d) thiazole-2-amine Example 4 was implemented with reference to the method of Example 1, and 2-chloro-4-(trifluoromethyl) benzo (d) thiazole was substituted for the 2-chloro-4-fluorobenzo (d) thiazole to yield a white solid 1.1 g (yield 67%).

¹H NMR (400 MHz, DMSO-d₆) δ 7.55 (d, J=5.8 Hz, 1H), 7.39 (d, J=7.9 Hz, 1H), 7.15-7.07 (m, 3H), 7.00 (d, J=8.0 Hz, 1H), 3.92 (s, 3H).

ESI-MS m/z: 382.1 ((M+H)$^+$).

Example 5

Preparation of N-(4-fluorobenzoyl (d) thiazole-2-group)-4,7-dimethoxy benzozoyl (d) thiazole-2-amine Example 5 was implemented with reference to the method of Example 1, and 4,7-methoxybenzo (d) thiazol-2-amine was substituted for the 4-methoxybenzo (d) thiazole-2-amine to yield a white solid 1.4 g (yield 73%).

¹H NMR (400 MHz, DMSO-d₆) δ 7.74 (d, J=5.8 Hz, 1H), 7.39 (d, J=7.9 Hz, 1H), 7.27-7.15 (m, 3H), 7.00 (d, J=8.0 Hz, 2H), 3.82 (s, 3H), 3.76 (s, 3H).

ESI-MS m/z: 362.1 ((M+H)$^+$).

Example 6

Preparation of N-(4-fluorobenzoyl (d) thiazole-2-group)-4,6-dimethoxy benzozoyl (d) thiazole-2-amine Example 6 was implemented with reference to the method of Example 1, and 4,6-nethoxybenzo (d) thiazol-2-amine was substituted for the 4-methoxybenzo (d) thiazole-2-amine to yield a white solid 1.2 g (yield 64%).

¹H NMR (400 MHz, DMSO-d₆) δ 7.75 (d, J=5.8 Hz, 1H), 7.28-7.17 (m, 2H), 7.21 (s, 1H), 6.79 (s, 1H), 3.88 (s, 3H), 3.83 (s, 3H).

ESI-MS m/z: 332.1 ((M+H)$^+$).

Example 7

Preparation of 4,7-dimethoxyn-(4-(trifluoromethyl) benzene (d) thiazole-2-group) benzene (d) thiazole-2-amine Example 7 was implemented with reference to the method of Example 1, and 2-chloro-4-(trifluoromethyl) benzo (d) thiazole was substituted for the 4-methoxybenzo(d) thiazole-2-amine to yield a white solid 0.9 g (yield 53%).

¹H NMR (400 MHz, DMSO-d₆) δ 7.75 (d, J=5.8 Hz, 1H), 7.49 (d, J=7.9 Hz, 1H), 7.28-7.17 (m, 1H), 7.00 (d, J=8.0 Hz, 2H), 3.92 (s, 3H).

ESI-MS m/z: 412.1 ((M+H)$^+$).

Example 8

Preparation of 4,6-dimethoxyn-(4-(trifluoromethyl) benzo (d) thiazole-2-group) benzo (d) thiazole-2-amine Example 8 was implemented with reference to the method of Example 1, and 2-chloro-4-(trifluoromethyl) benzo (d) thiazole was substituted for the 2-chloro-4-fluorobenzo (d) thiazole, and 4,6-methoxybenzo (d) thiazol-2-amine was substituted for the 4-methoxybenzo (d) thiazole-2-amine to yield a white solid 0.8 g (yield 47%).

¹H NMR (400 MHz, DMSO-d₆) δ 7.75 (d, J=5.8 Hz, 1H), 7.49 (d, J=7.9 Hz, 1H), 7.28-7.17 (m, 1H), 7.21 (s, 1H), 7.69 (s, 1H), 3.92 (s, 3H).

ESI-MS m/z: 412.1 ((M+H)$^+$).

Example 9

Preparation of Pharmaceutical Composition: Tablet Form 1 g of the antitumor compounds having the structure of Formula I, or the pharmaceutical salts thereof was mixed with 23 g of lactose and 5.7 g of microcrystalline cellulose by using a mixer, followed by compression or molding of the resulting mixture with a roller compactor, thereby acquiring a disk-shaped compressed solid. A hammer mill is used to shred or crush the disk-shaped compressed solid into a powder with a predefined particle size allowing to pass through a 20-mesh sieve. 0.3 g of precipitated silica and 0.3 g of magnesium stearate were added to the powder that has been passed through the sieve, mixed thoroughly, and pressed from the powder into a tablet form using a roller compactor.

The antitumor compounds having the structure of Formula I can be selected from the group consisting from the compounds prepared in Examples 1-8.

The acid radicals of the pharmaceutical salts come from the group consisting of hydrochloric acid, sulfuric acid, benzenesulfonic acid, p-toluenesulfonic acid, phosphoric acid, hydrobromic acid, maleic acid, fumaric acid and malic acid.

Example 10

Preparation of Pharmaceutical Composition: Gelatin Capsule 1 g of the antitumor compounds having the structure of Formula I, or the pharmaceutical salts thereof was mixed with 0.15 g of lactose, 0.35 g of microcrystalline cellulose and water to produce a granular material. 0.04 g of croscarmellose sodium and 0.01 g of magnesium stearate were added to the granular material, mixed thoroughly, and filled into gelatin capsules, thereby allowing the gelatin capsules to be taken orally (The gelatin capsules of Example 10 meet medical standards and were purchased from Suzhou Capsule Co., Ltd. of China). The antitumor compounds having the structure of Formula I can be selected from the group consisting of the compounds prepared in Examples 1-8.

The acid radicals of the pharmaceutical salts come from the group consisting of hydrochloric acid, sulfuric acid, benzenesulfonic acid, p-toluenesulfonic acid, phosphoric acid, hydrobromic acid, maleic acid, fumaric acid and malic acid.

Example 11

Comparison of the biological activity of bisbenzothiazolamide compounds:

The synthesized compounds of Examples 1-8 were numbered consecutively, including JAC1, JAC1011, JAC1012, JAC1013, JAC1014, JAC1015, JAC1016, and JAC1017. High-throughput screening (HTS) was used to identify the human bronchial epithelial (HBE) cells stably transfected with a DNA construct with a luciferase gene under control of a 2,000 bp long promoter of JWA gene. After HTS two times, the compound had a concentration ranging from 0.00 g/mL-3.30 g/mL to which the living cells were exposed for 48 h. Table 1 showed the results of the fluorescence intensity of the reporter gene whose expression was influenced by the eight representative compounds.

Referring to Table 1, the eight compounds activate JWA gene of the HBE cells, leading to a clear dose-effect relationship where JAC1 has a particularly significant effect on activation of JWA gene.

FIG. 1 is a sequence containing the 2000 bp promoter sequence of JWA gene that was used for a luciferase reporter gene plasmid construction. FIG. 2 shows the molecular structure of a luciferase reporter gene plasmid containing the promoter sequence of JWA gene.

Example 12

Effect of JAC1 on the Colony Formation (Malignant Proliferation) of HER2-Positive Breast Cancer Cells Example 12 was implemented to determine the effect of treatment with small-molecule compound JAC1 on the colony formation (malignant proliferation) of breast cancer cells overexpressing HER2 protein.

Two human breast cancer cell lines BT474 and SKBR3 were incubated in DMEM medium containing, respectively, 20% and 10% fetal bovine serum (FBS), conventional double-antibody, and were placed in a 37° C. incubator with 5% $CO_2$. The BT474 and SKBR3 cells in the logarithmic growth phase were transferred into 6-well plates for 800 cells per well. After the cells adhered to the walls of the plates, the cells were cultured in the medium containing different concentrations (0, 1, and 10 μM) of JAC1, respectively. By observing the formation of each cell colony, the cells were continued to be cultured for 10-15 d, followed by removal of medium. After fixation with methanol and photographing, the number of the cell colonies (each containing more than 50 cells) was counted using the software ImageJ, and the computer program SPSS is used for statistical analysis.

Figure 3A:
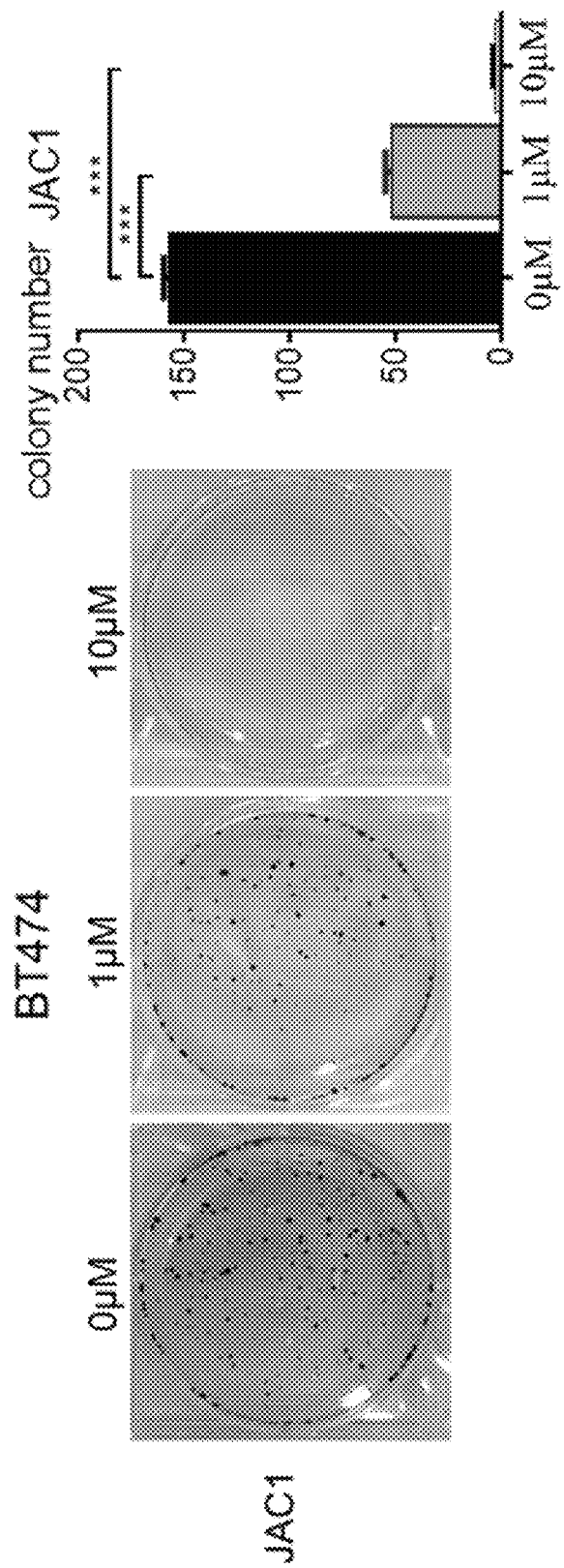
FIGS. 3A-3B are results of the effect of JAC1 on the malignant clone of human breast cancer cells in accordance with Example 12 of the disclosure.
Figure 3B:
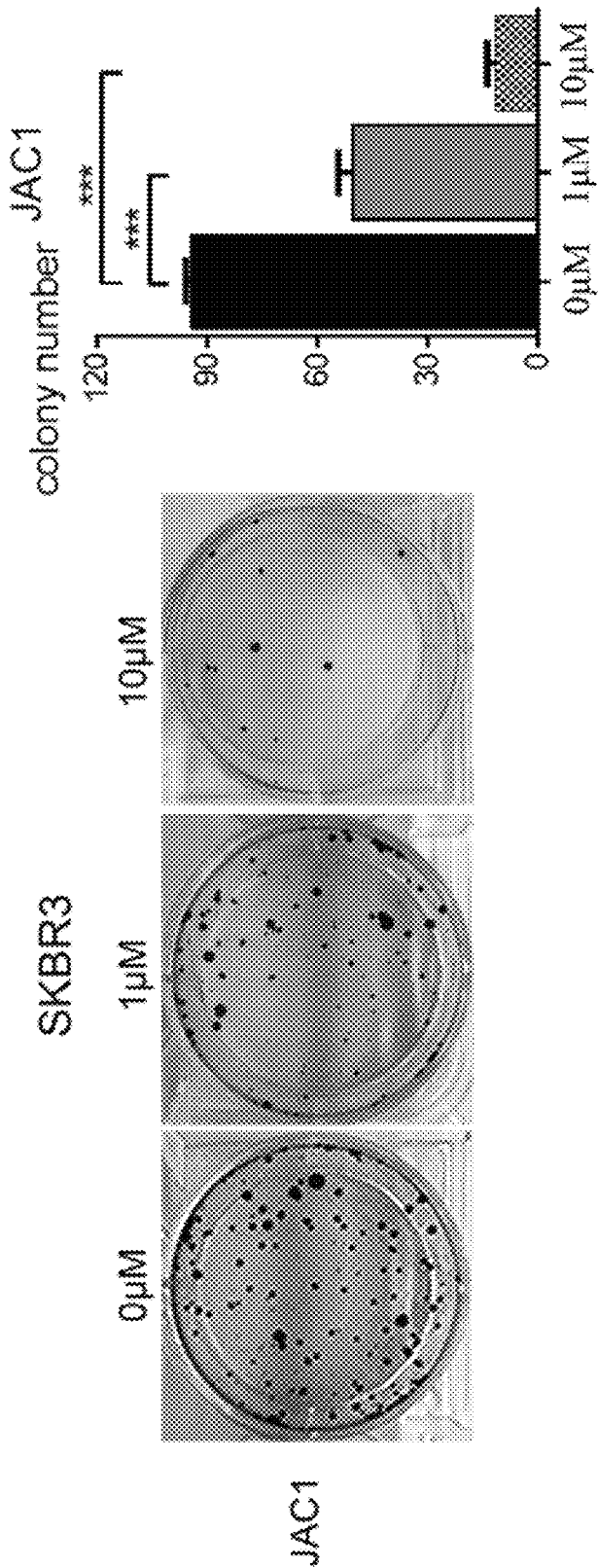

Referring to FIG. 3, when compared to control group, different doses of the small-molecule compound JAC1 can significantly reduce the colony-forming ability of BT474 and SKBR3 cells, leading to a dose-effect relationship.

Note: the other compounds prepared in Examples 1-8 were undergone the colony-forming assay with reference to the method of Example 12. The results were consistent with each prepared compound that significantly reduced the colony-forming ability of BT474 and SKBR3 cells, leading to a dose-effect relationship.

TABLE 1

Bisbenzothiazolamide compounds and fluorescence intensity of reporter gene thereof

| Concentration μg/mL | JAC1 | JAC1 011 | JAC1 012 | JAC1 013 | JAC1 014 | JAC1 015 | JAC1 016 | JAC1 017 |
|---|---|---|---|---|---|---|---|---|
| 0.00 | 12053.33 | 12126.67 | 12580.00 | 12687.67 | 12614.67 | 13050.00 | 12696.67 | 12440.00 |
| 0.05 | 13560.00 | 13255.33 | 13448.67 | 13315.33 | 13835.33 | 14335.33 | 14360.00 | 12910.00 |
| 0.10 | 16200.00 | 13553.33 | 13518.67 | 12346.00 | 14254.00 | 15573.33 | 16238.00 | 13086.67 |
| 0.21 | 21975.00 | 15397.33 | 16205.00 | 14926.00 | 15262.67 | 18260.67 | 19226.00 | 14460.00 |
| 0.41 | 28186.67 | 19835.00 | 19768.67 | 16036.67 | 18680.00 | 22168.67 | 24518.00 | 17188.00 |
| 0.83 | 38760.00 | 25886.67 | 25237.33 | 20014.00 | 22088.00 | 28162.67 | 28746.00 | 22680.00 |
| 1.65 | 54293.33 | 31413.33 | 33228.00 | 26261.67 | 28702.00 | 30168.67 | 32253.33 | 28406.00 |
| 3.30 | 68080.00 | 39676.33 | 41139.33 | 35332.33 | 37664.67 | 37663.33 | 36361.67 | 37426.00 |

TABLE 2

Number given to the Bisbenzothiazolamide compounds

| No. | Compounds |
|---|---|
| JAC1 | 4-fluoro-N-(4-methoxy benzene (d) thiazole-2-group) benzene (d) thiazole-2 - amine |
| JAC1011 | 4,7-difluoro-n-(4-methoxybenzo-thiazole-2-group) benzoylthiazole-2-amine |
| JAC1012 | 4,6-difluoro-n-(4-methoxylbenzene (d) thiazole-2-group) benzene (d) thiazole-2-amine |
| JAC1013 | 4-methoxy-N-(4-(trifluoromethyl) benzo (d) thiazole-2-group) benzo (d) thiazole-2-amine |
| JAC1014 | N-(4-fluorobenzoyl (d) thiazole-2-group)-4,7-dimethoxy benzozoyl (d) thiazole-2-amine |
| JAC1015 | N-(4-fluorobenzoyl (d) thiazole-2-group)-4,6-dimethoxy benzozoyl (d) thiazole-2-amine |
| JAC1016 | 4,7-dimethoxyn-(4-(trifluoromethyl) benzene (d) thiazole-2-group) benzene (d) thiazole-2-amine |
| JAC1017 | 4,6-dimethoxyn-(4-(trifluoromethyl) benzo (d) thiazole-2-group) benzo (d) thiazole-2-amine |

Example 13

Effect of JAC1 on the Cellular Location of HER2 Protein in HER2-Positive Breast Cancer Cells Example 13 was implemented to determine the effect of treatment with small-molecule compound JAC1 on the cellular localization of HER2 protein in cells.

The cells were inoculated into a 35 mm glass bottom dish, treated with different concentrations (0, 1, and 10 μM) of JAC1 for 24 h, fixed with methanol for 15 min, washed three times with PBST, blocked with normal sheep serum for 1 h, and incubated in primary antibody overnight at 4° C. The cells were then washed three times with PBST, incubated in fluorescent secondary antibody and 4',6-diamidino-2-phenylindole (DAPI), and photographed using a laser confocal scanning microscopy.

Figure 4A:
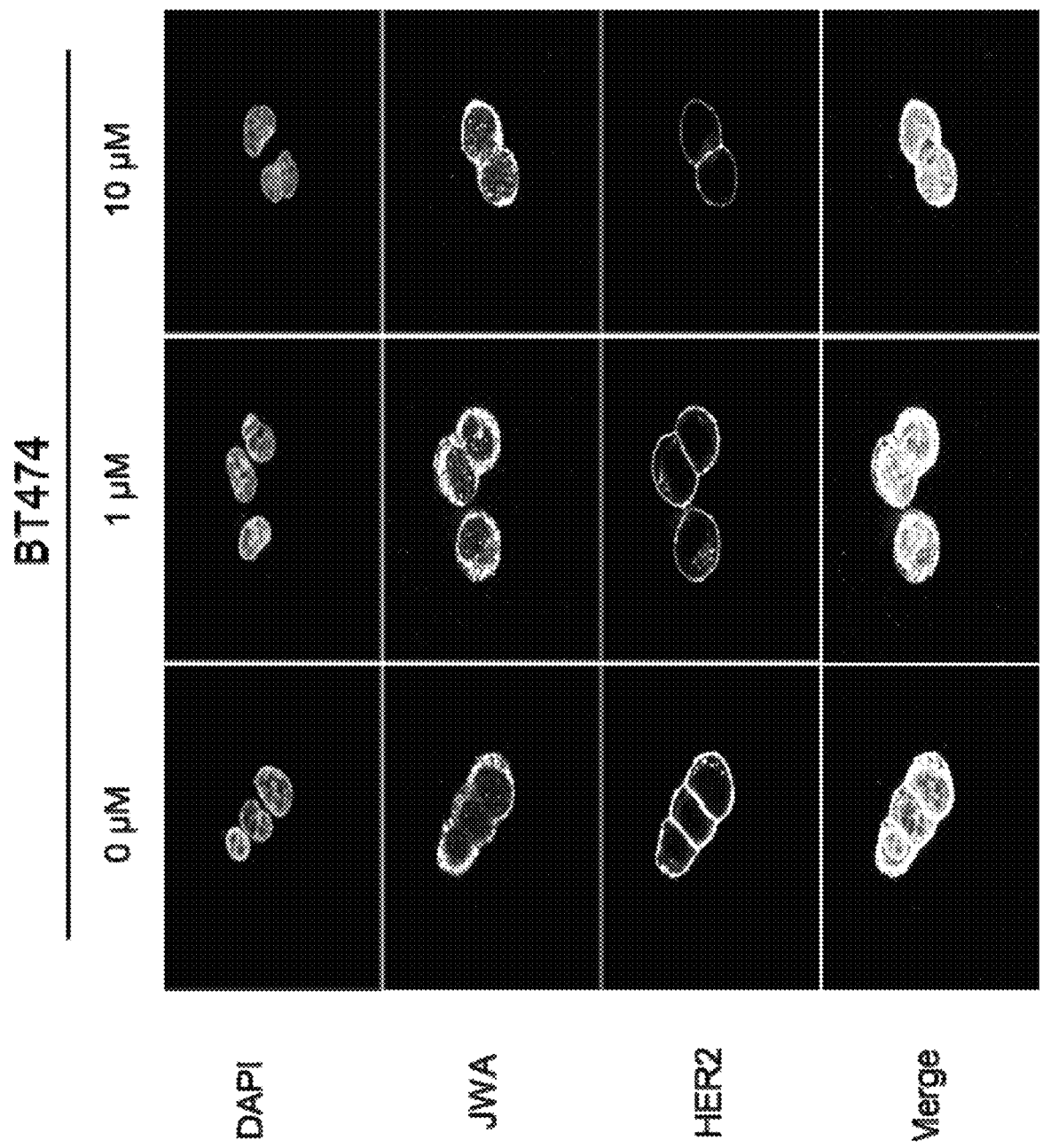
FIG. 4A-4B are results of the effect of JAC1 on the cellular localization and HER2 expression level of human breast cancer cells in accordance with Example 13 of the disclosure.
Figure 4B:
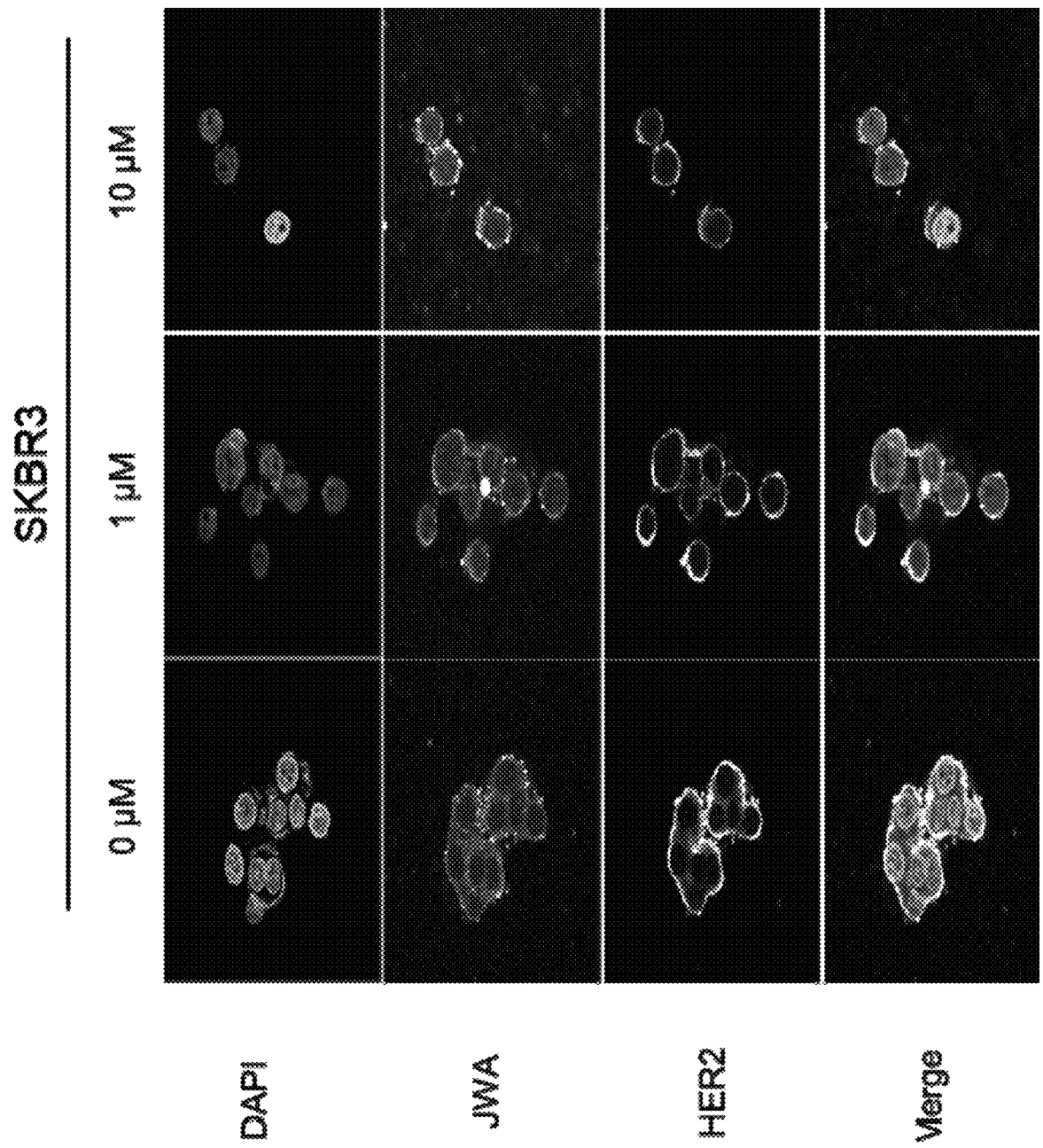

Referring to FIG. 4, the JWA protein level increased and the HER2 protein level reduced with increasing concentration of JAC1, and HER2 protein was localized to the cell membrane even if JAC1 causes a decrease in the level of HER2 protein. In conclusion, JAC1 has no effect on the localization of HER2 protein in the cell membrane.

Note: the other compounds prepared in Examples 1-8 were undergone the cellular localization with reference to the method of Example 13. The results are consistent with JAC1 that JWA protein level increased and the HER2 protein level reduced with increasing concentration of JAC1, and HER2 protein was localized on the cell membrane despite the fact that each compound caused a decrease in the level of HER2 protein. In conclusion, JAC1 had no effect on the localization of HER2 protein at the cell membrane.

Example 14

Effect of JAC1 on the Expression Levels of JWA and HER2 Proteins in HER2-Positive Breast Cancer Cells.

Example 14 was implemented to determine the effect of treatment with JAC1 on the increase in JWA protein level and the decrease in HER2 protein level verified using a cell culture model.

The cells in the logarithmic growth phase were routinely digested, and transferred into 6-well plates at the cell density of 40%-50%. The cells were incubated with different concentrations of JAC1 for 24 h, followed by an addition of 0.1 mL of Radioimmunoprecipitation Assay Butter (RIPA, containing 0.5% phenylmethylsulfonyl fluoride (PMSF)) for protein extraction. After centrifugation at 12,000×g for 15 min, the supernatant was collected, and brought to a determination of protein concentration and a boil. Protein electrophoresis was performed with 10% polyacrylamide gel. The protein was transferred into the gel wells for 40 μg protein per well, migrated at 60 V for 30 min, and 90 V for 1.5-2 h. After gel electrophoresis, the protein was transferred by wet method from gel to a PVDF membrane, and blocked with 5% skim milk at room temperature for 1-2 h. The membrane was washed with Tris-Buffered Saline and Tween 20 (TBST, containing 0.1% Tween 20) three times for 5 min each, and incubated in the corresponding primary antibody overnight at 4° C. The membrane was then washed with the TBST (containing 0.1% Tween 20) three times for 5 min each, incubated in the secondary antibody at room temperature for 1-2 h, and washed with the TBST (containing 0.1% Tween 20) eight times for 5 min each. Electrochemiluminescence (ECL) solution was dropped to cover the membrane, followed by exposure for a certain time.

Figure 5:
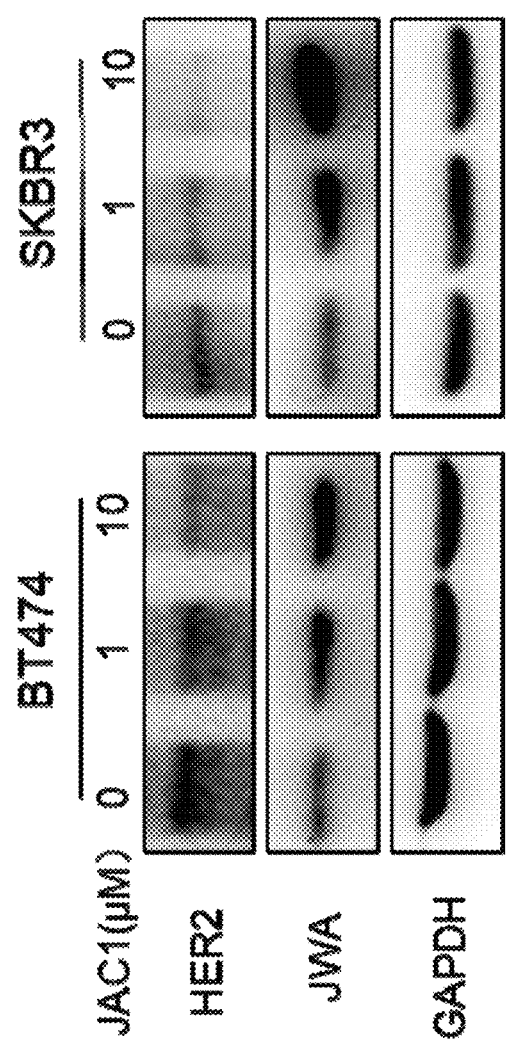
FIG. 5 is a result of the effect of JAC1 on the expression levels of JWA and HER2 proteins in breast cancer cells in accordance with Example 14 of the disclosure.

Referring to FIG. 5, the JWA protein level increased and the HER2 protein level decreases with increasing concentration of JAC1.

Note: the other compounds prepared in Examples 1-8 were undergone the western blot with reference to the method of Example 14. The results are consistent with JAC1 that the JWA protein level increased and the HER2 protein level decreases with increasing concentration of each prepared compound.

Example 15

Effect of JAC1 on the Migratory Ability of HER2-Positive Breast Cancer Cells.

Example 15 was implemented to determine the effect of JAC1 on the migratory ability of breast cancer cells BT474 and SKBR3 through Transwell migration assay.

BT474 and SKBR3 cells in the logarithmic growth phase were transferred into six-well plates at the cell density of 40%-50%. After the cells adhered to the walls of the plates, the cells were respectively incubated in 0, 1, and 10 μL of JAC1. Spreading gel in Transwell chamber: the day before the assay, a 24-well plate and a plurality of Transwell chambers were prepared, and 1 mg/mL fibronectin (FN) mother liquor was diluted 10 times to a final concentration of 100 μg/mL. The bottom of each Transwell chamber was coated with 50 μL of FN, placed on a clean bench to air-dry for 2 h, and cultured in an incubator overnight.

On the day of the assay, the cultured cells were digested with 0.25% trypsin and resuspended in a serum-free medium in which the number of the cells were counted and the cell density was adjusted to $3\times10^5$ cells/mL. 100 μL of serum-free medium containing the cells was transferred onto the upper layer of each Transwell chamber, and 600 μL of mixture containing 10% FBS and 100 ng/mL EGF medium was added to the lower layer of each Transwell chamber. After incubation in an incubator for 12 h, the Transwell chambers were taken out, fixed with 95% methanol for 20 min, washed three times with phosphate-buffered saline (PBS), stained with crystal violet dye for 30 min, and washed three times with PBS. The cells adhered to the Transwell chambers were gently wiped from the upper layer of each Transwell chamber with a cotton swab. Each Transwell chamber was placed on a glass slide, observed using an inverted microscope through which images were photographed on the top, bottom, left, right and middle of each Transwell chamber. The number of the cells passing through the Transwell chamber was counted and used to perform the statistical analysis.

Figure 6A:
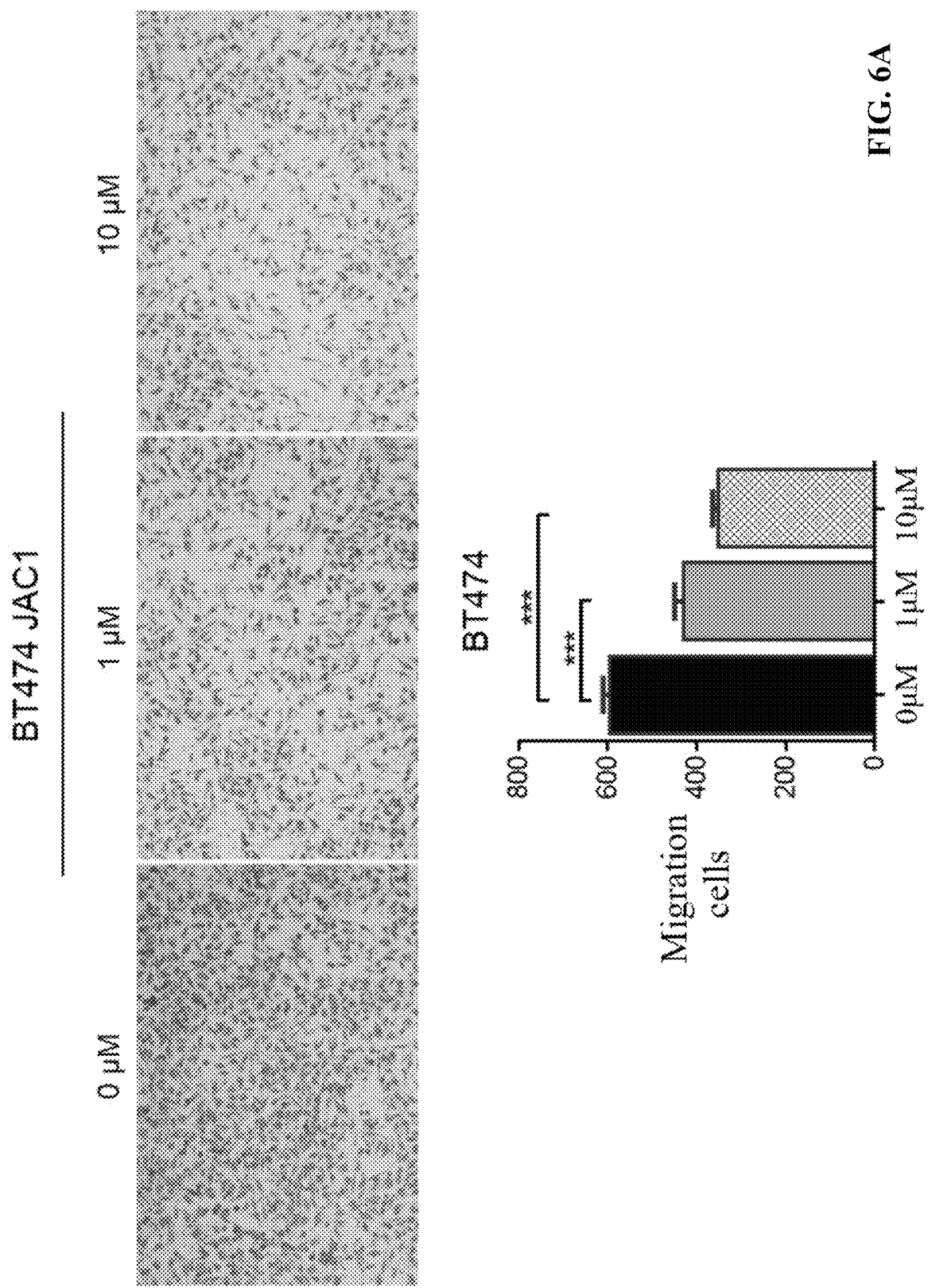
FIG. 6A-6B are results of the effect of JAC1 on the migratory ability of breast cancer cells BT474 and SKBR3 in accordance with Example 15 of the disclosure.
Figure 6B:
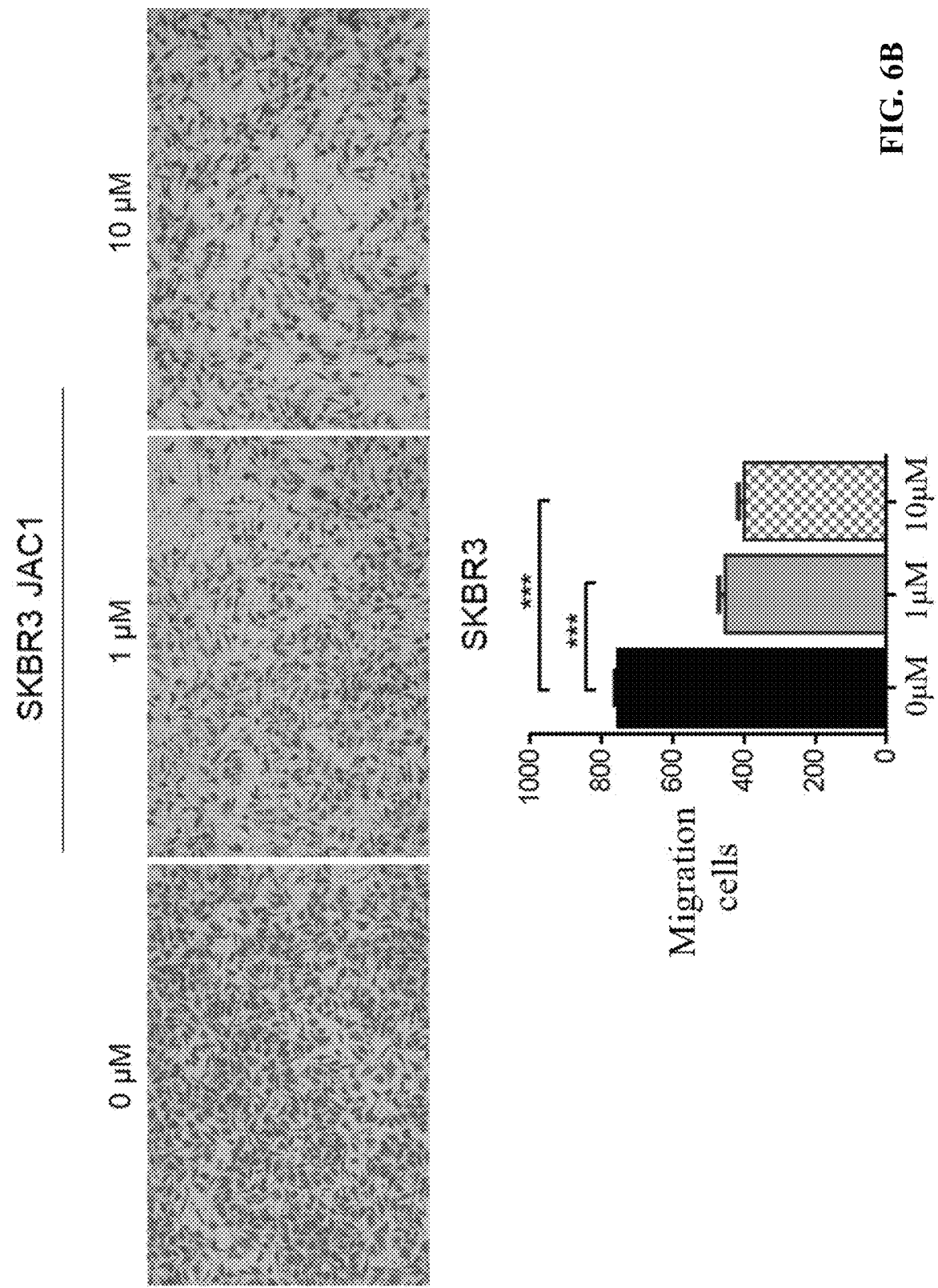

Referring to FIG. 6, JAC1 can effectively inhibit the migratory ability of cancer breast cells BT474 and SKBR3, leading to a dose-effect relationship.

Note: the other compounds prepared in Examples 1-8 were undergone the Transwell cell migration assay with reference to the method of Example 15. The results are consistent with JAC1 that can effectively inhibit the migratory ability of cancer breast cells BT474 and SKBR3, leading to a dose-effect relationship.

Example 16

Effect of JAC1 on Tumor Growth in a Model of Nude Mice Subcutaneously Transplanted with HER2-Positive Human Breast Cancer Cells.

Example 16 was implemented to build a model of nude mice subcutaneously transplanted with HER2-positive human breast cancer cells, contributing to determine the effect of JAC1 on tumor growth in the subcutaneous space of the mouse after implantation.

BT474 human breast cancer cells in the logarithmic growth phase were suspended in ice-cold suspension buffer for a final concentration of $5\times10^6/100$ μL, followed by subcutaneous transplantations of the suspended cells into BALB/c nude mice. When the tumor grown up to 75-125 mm$^3$, the BALB/c nude mice were randomly divided into five equal groups, including a blank control group (Mock), a solvent control group (Vehicle), a 50 mg/kg JAC1 treatment group, a 100 mg/kg JAC1 treatment group, and a positive control group treated with Pacilitaxel and Trastuzumab (TH). Dose and administration: JAC1 was injected intraperitoneally into mice once daily; the dosage of Trastuzumab was 10 mg/kg injected intraperitoneally twice a week; the dosage of Pacilitaxel was 20 mg/kg injected intraperitoneally once a week. From the day of administration, mouse body weights and tumor diameters were measured every other 2 days, and the tumor volume was calculated using an equation. When the mice reached a humane endpoint at which the tumor volume increased to 2500-3000 mm$^3$, the research based on the mouse models was terminated and the laboratory mice were anesthetized and euthanized in a timely manner to alleviate animal suffering and perform the statistical analysis.

Figure 7:
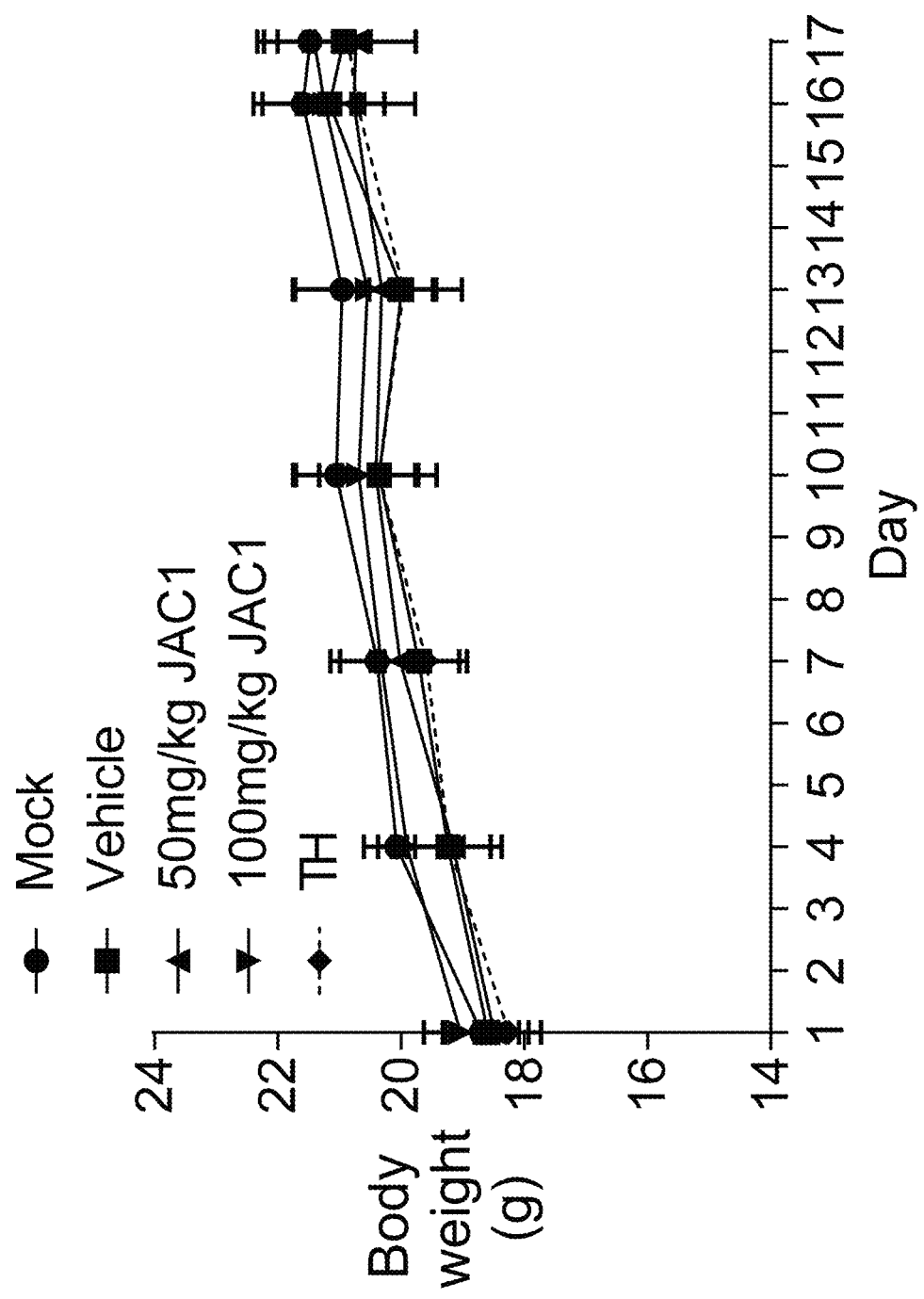
FIG. 7 is a graph of body weight curve of nude mice subcutaneously transplanted with human breast cancer cells BT474 in accordance with Example 16 of the disclosure.

Analysis of the results showed that the mouse body weight exhibited a slow increasing trend throughout which stages of measurement (FIG. 7).

Figure 8:
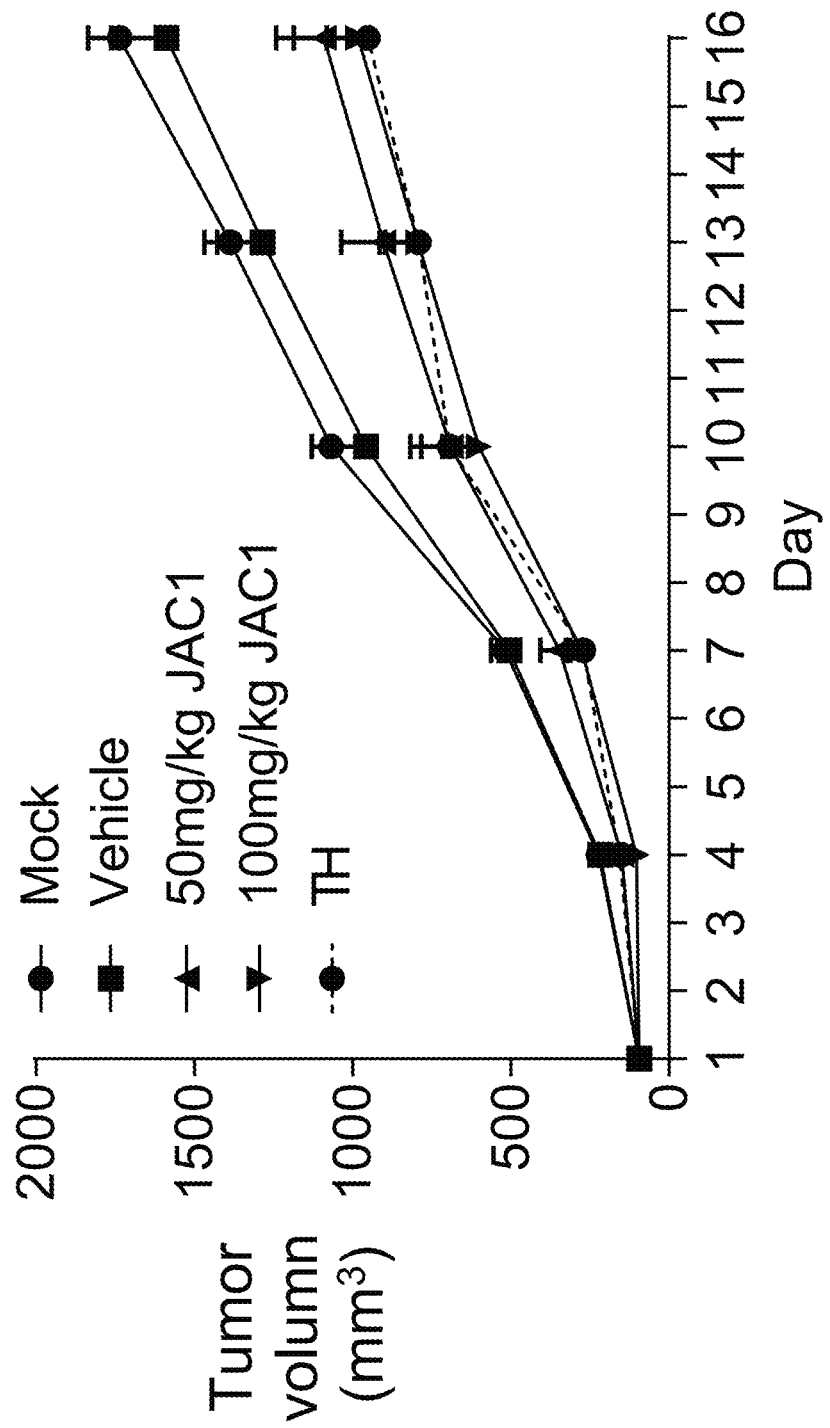
FIG. 8 is a graph of tumor volume curve of nude mice subcutaneously transplanted with human breast cancer cells BT474 in accordance with Example 16 of the disclosure.
Figure 9:
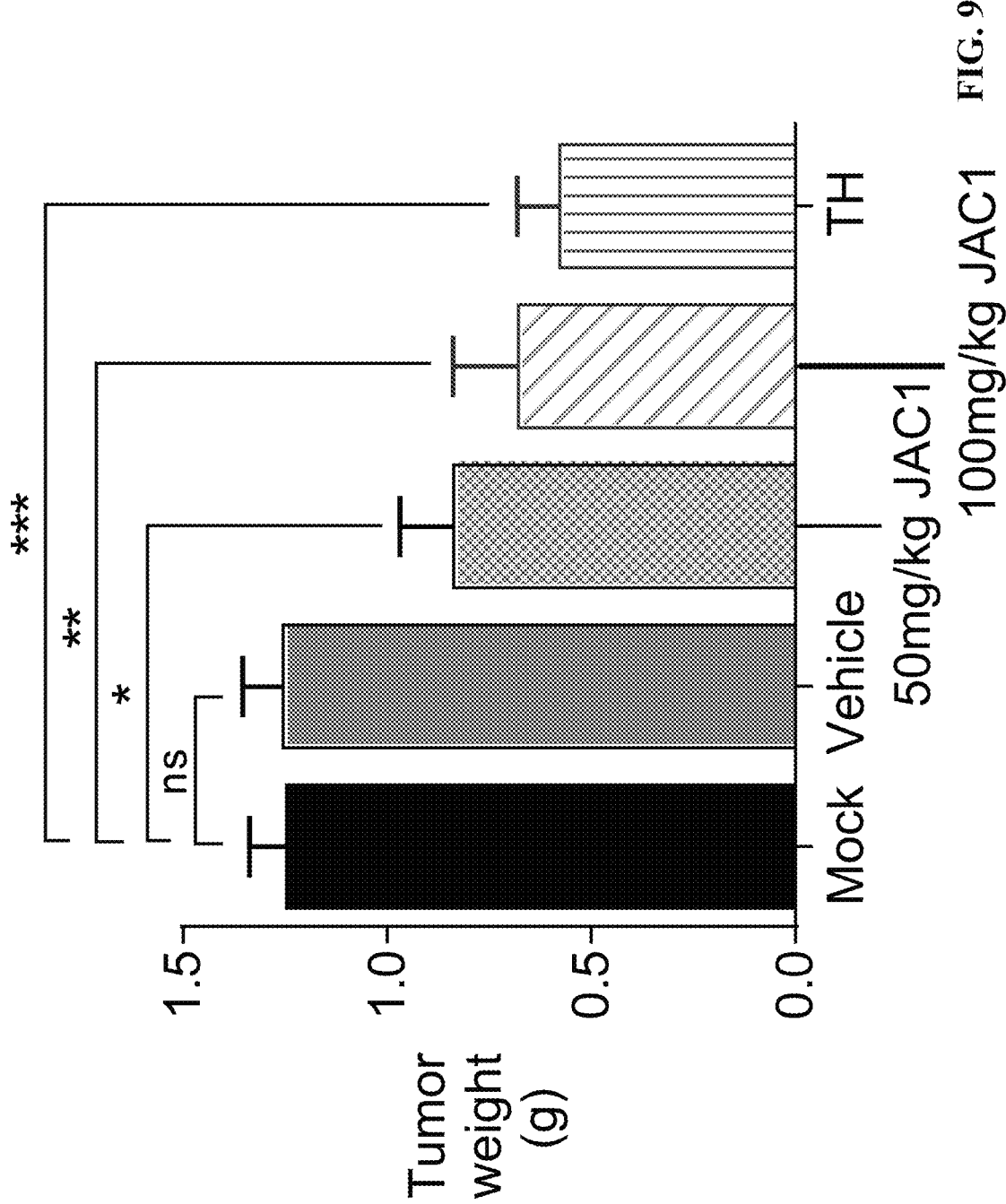
FIG. 9 is a result of tumor weights of nude mice subcutaneously transplanted with human breast cancer cells BT474 in accordance with Example 16 of the disclosure.
Figure 10:
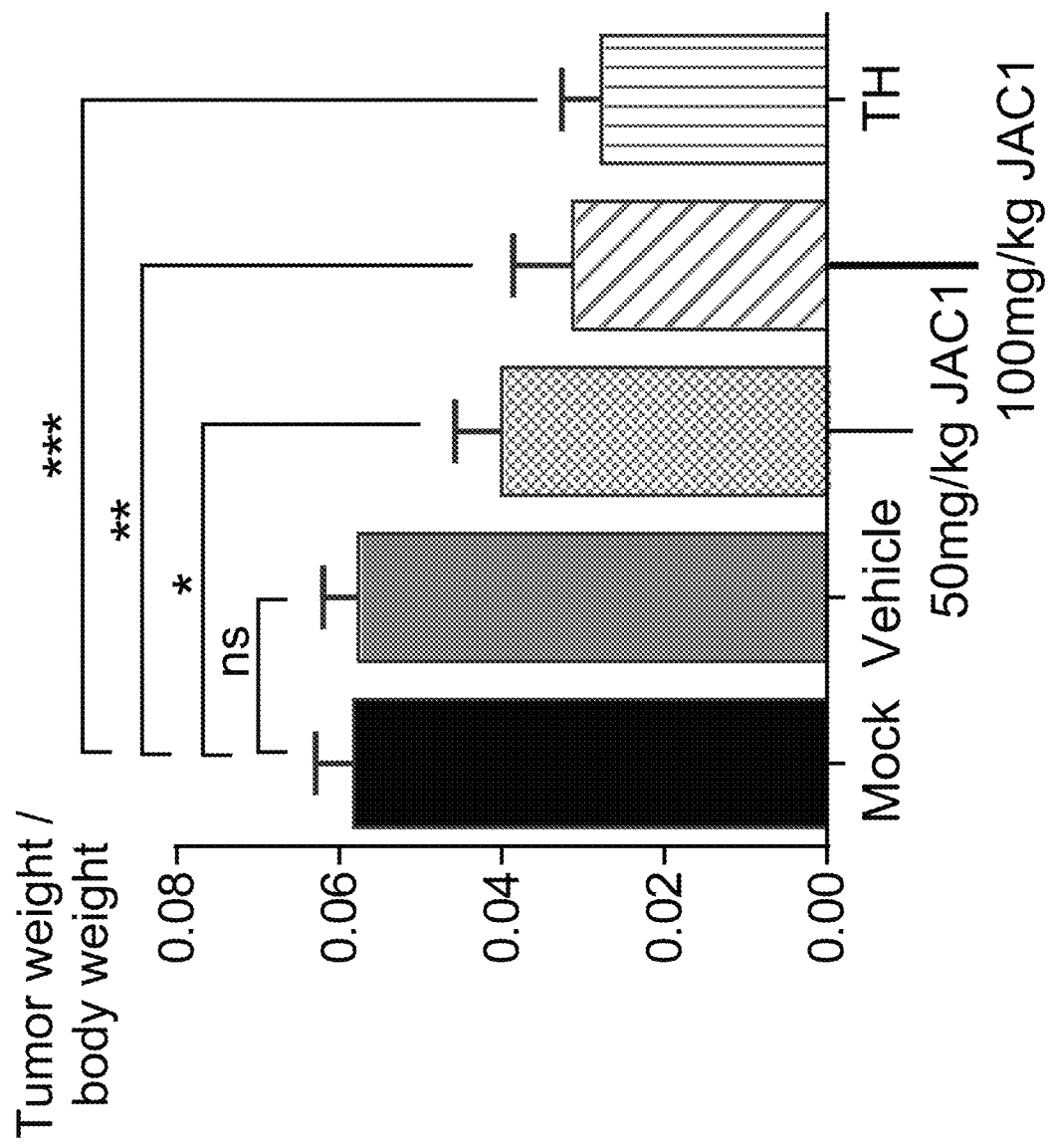
FIG. 10 is a result of tumor weight/mouse body weight ratio of nude mice subcutaneously transplanted with human breast cancer cells BT474 in accordance with Example 16 of the disclosure.

When compared with the blank control group, the obvious results at suppressing tumor growth were achieved in the 50 mg/kg JAC1 treatment group, the 100 mg/kg JAC1 treatment group, and the TH group (FIG. 8). In the three groups the tumor weights were reduced (P<0.05), and the average tumor weight: TH group <100 mg/kg JAC1 treatment group <50 mg/kg JAC1 treatment group (FIG. 9). The tumor weight/mouse body weight ratios decreased (P<0.05) in the three groups among which the TH group shows the lowest ratio (FIG. 10).

Figure 11:
FIG. 11 shows the tumor tissues isolated from nude mice subcutaneously transplanted with human breast cancer cells BT474 in accordance with Example 16 of the disclosure.

FIG. 11 is a schematic diagram of the tumor tissue isolated from each group of mice.

Figure 12:
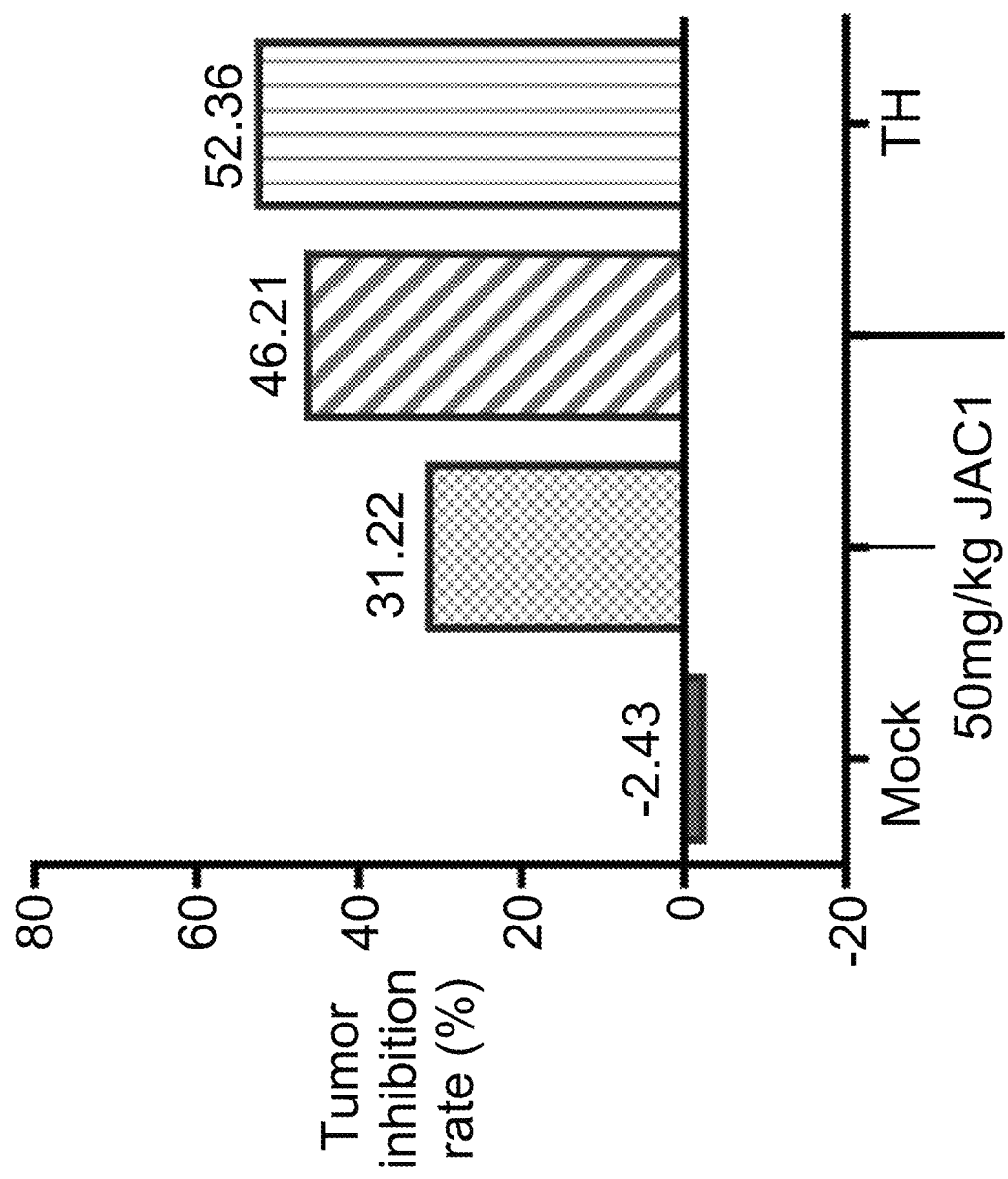
FIG. 12 is a graph of the tumor growth inhibition rate of each group of mice in accordance with Example 16 of the disclosure.

Tumor growth inhibition rate: TH group (52.36%)>100 mg/kg JAC1 group (46.21%)>50 mg/kg JAC1 group (31.22%) (FIG. 12); the results indicated that TH, 100 mg/kg JAC1, and 50 mg/kg JAC1 were effective substances to inhibit the growth of tumor.

Figure 13:
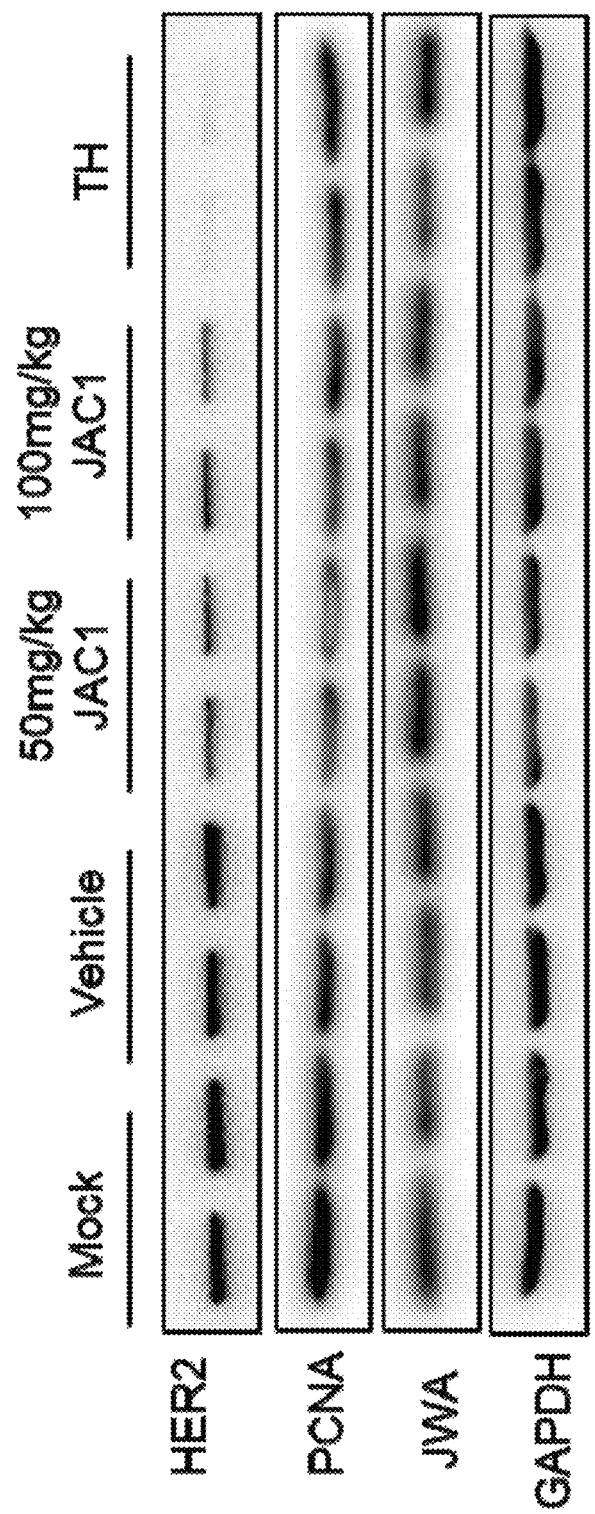
FIG. 13 is a graph of the expression levels of related proteins of each group of mice in accordance with Example 16 of the disclosure.

Further, western blotting technology was used to test the expression level of related proteins of breast cancer cells in the subcutaneous space of mouse after implantation. Referring to FIG. 13, in the JAC1 treatment group, the HER2 protein level was repressed significantly, while, conversely, the JWA protein level significantly increased; the HER2 protein of the TH group was not being detected in western blot because the Trastuzumab was a humanized anti-HER2 antibody that first bounds to the epitopes on the HER2 protein before the primary antibody recognized the HER2 protein.

Example 17

Effect of JAC1 on the Major Organ Structures in a Model of Nude Mice Subcutaneously Transplanted with Human Breast Cancer Cells.

Figure 14:
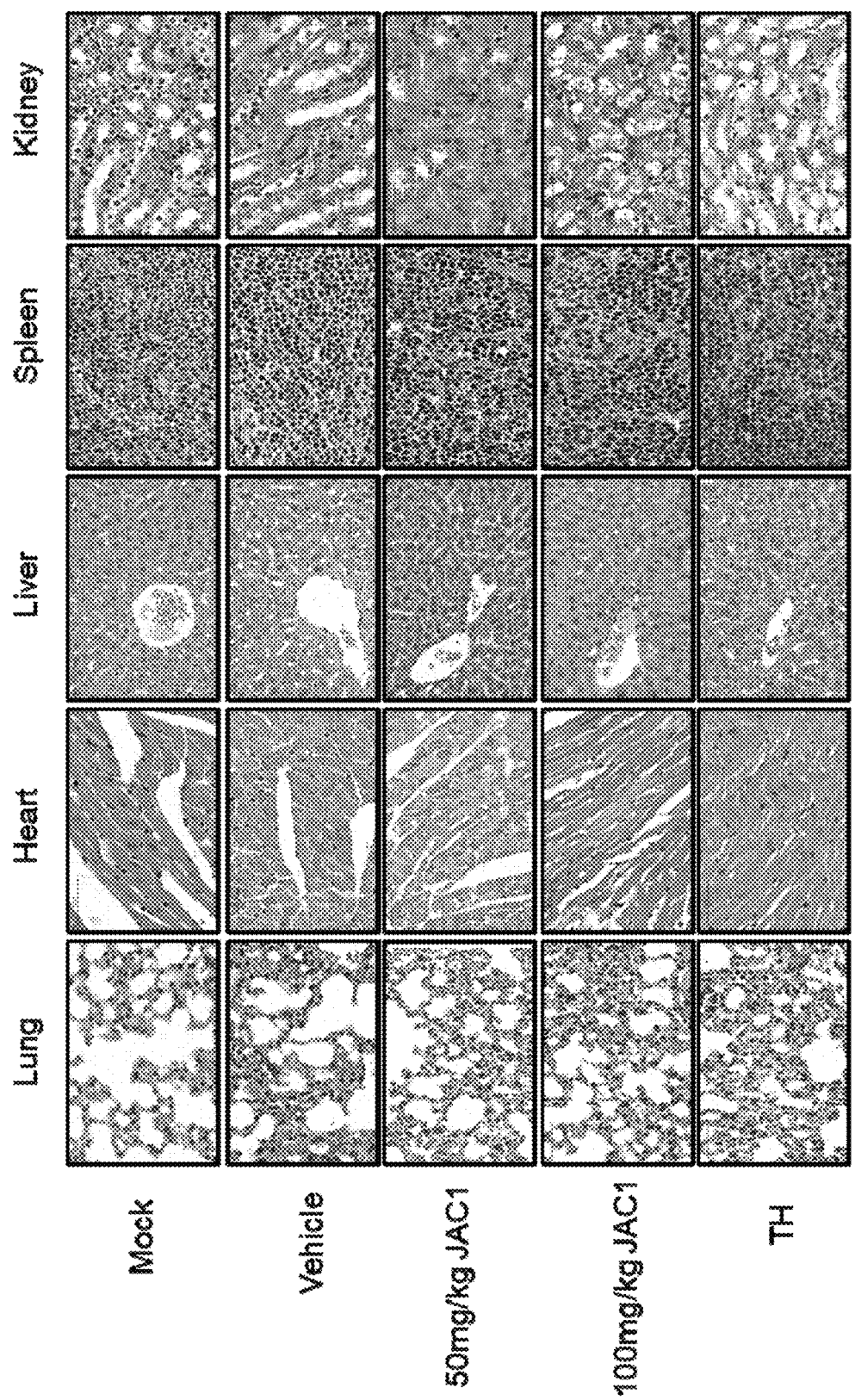
FIG. 14 is a H&E-stained image of JAC1 acting on major organs of nude mice subcutaneously transplanted with human breast cancer cells in accordance with Example 17 of the disclosure.

A model of nude mice subcutaneously transplanted with human breast cancer cells was built with reference to the method of Example 16. The laboratory mice that have been modeled were anesthetized and euthanized to observe and determine whether damage occurred to the major organs of laboratory mice. The major organs tissues from the laboratory mice, such as heart, liver, spleen, lung, kidney, and brain, were fixed in formalin solution using conventional methods. After paraffin embedding and tissue sectioning, the thick tissue sections were stained with H&E to observe whether the organ tissues were normal in morphology. The results indicated that no obvious anomalies were observed in the major organs (including heart, liver, spleen, lung, kidney, and brain) of laboratory mice under a microscope (FIG. 14).

Example 18

Effect of JAC1 on the Serum Biochemical Indexes in a Model of Nude Mice Subcutaneously Transplanted with Human Breast Cancer Cells.

A model of nude mice subcutaneously transplanted with human breast cancer cells was built with reference to the method of Example 16. The laboratory mice that have been modeled were anesthetized to determine whether damage occurred to the major organs in the mouse body. Whole blood was collected from the anesthetized mice, and the serum was separated and used to detect a change in the serum biochemical indexes using an automatic biochemistry analyzer. Referring to FIG. 15, the results indicated that no obvious morphological anomalies were observed in the structures of the major organs in laboratory mice. When compared with the blank control group, the JAC1 treatment groups, particularly the 100 mg/kg JAC1 caused significant decreases in aspartate transaminase (AST), alanine transaminase (ALT), triglyceride (TG), and creatine kinase (CK) and the isoenzyme thereof (CKMB), and AST and ALT are used to test liver function. Conversely, the level of superoxide dismutase (SOD) as an antioxidant enzyme significantly increased. The changes in blood biochemical indicators of the TH group were associated with a trend toward slight improvement compared with the blank control group, while showing no statistically significant difference between the two groups.

The results indicated that JAC1 can effectively inhibit the growth of tumor formed by human breast cancer cells BT474 in the subcutaneous space of mice after implantation, and also provide an in vivo intervention in the biochemical dysfunction caused by tumors. The TH group had a slight, but not significant, in vivo effect on improving biochemical dysfunction caused by the tumors, despite the fact that the TH group had a higher tumor growth inhibition rate than the JAC1 treatment groups.

Example 19

Detection of Off-Target Effects Occurring when JAC1 Activates JWA Protein and Represses HER2 Protein.

The disclosure further detected the off-target effects of tumor suppression by JAC1, after proving the effectiveness of treatment with the small molecule JAC1 to specifically inhibit the growth of cancer cells overexpressing HER2 protein. A HER2-positive BGC823 human gastric cancer cell line was established in which JWA gene was deleted using Crisp/cas9 technology. The BGC823 human gastric cancer cell line (JWA WT) with JWA gene, and a BGC823 human gastric cancer cell line (JWA KO) without JWA gene (both of which had been proved to be HER2-positive), were treated with 10 μM JAC1 for 48 h. After protein extraction, western blotting technology was used to determine the expression levels of JWA and HER2 proteins in the wild-type cell line (JWA WT) and the JWA-knockout cell line (JWA KO).

Figure 16:
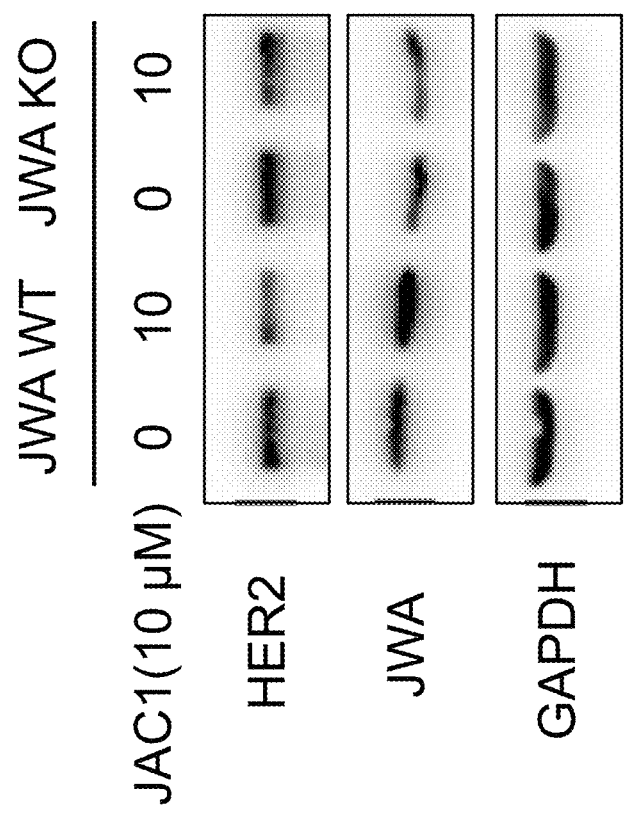
FIG. 16 is an image of off-target effects occurring when JAC1 activates JWA protein and represses HER2 protein in accordance with Example 19 of the disclosure.

Referring to FIG. 16, JAC1 treatment can significantly increase JWA protein level and repress HER2 expression in the wild-type gastric cancer cell (JWA WT). However, the JWA-knockout cell line (JWA KO) received a JAC1 treatment, which had no effect on the expression levels of JWA and HER2.

The results indicated that the inhibition effect of JAC1 on HER2 was achieved by activating JWA protein with no detectable off-target effects.

Example 20

Example 11 of the disclosure identified multiple compounds capable of activating JWA gene in cells by using high-throughput screening. Except for the compounds detailed in Examples 1-8, the other compounds were as follows: $R^1$=OH, $R^2$=H or OH, $R^3$=F or Cl, $R^4$=H or F, $R^5$=H, $CH_3$ or $CH_2CH_3$;

$R^1$=$CH_3$, $R^2$=$CH_3$ or $CH_2CH_3$, $R^3$=I or $CF_3$, $R^4$=Br or $CF_3$, $R^5$=H, $CH_3$ or $CH_2CH_3$;

$R^1$=$CH_2CH_3$, $R^2$=$CH_2CH_2CH_3$ or $OCH_3$, $R^3$=Br or Cl, $R^4$=Cl or I, $R^5$=H, $CH_3$ or $CH_2CH_3$;

$R^1$=$OCH_3$, $R^2$=$OCH_2CH_3$ or OH, $R^3$=F or $CF_3$, $R^4$=H or $CF_3$, $R^5$=H, $CH_3$ or $CH_2CH_3$;

$R^1$=$OCH_2CH_3$; $R^2$=$CH_3$ or $OCH_3$, $R^3$=Cl or I, $R^4$=Br or I, $R^5$=H, $CH_3$ or $CH_2CH_3$.

When a substituent was placed on different positions on each of the above compounds, or the same molecular formula forms different isomers, all of the structural compounds were included within the category of the prepared compounds of the disclosure.

The above compounds can activate JWA gene expression, having a prospect of preparation of JWA gene activators or antitumor drugs. Therefore, the compounds should be included in the protection scope of the disclosure.

The compounds of the disclosure can also enhance the effectiveness of treatment for malignant tumor when used in combination with other drugs and other treatment methods.

It will be obvious to those skilled in the art that changes and modifications may be made, and therefore, the aim in the appended claims is to cover all such changes and modifications.

What is claimed is:

1. A compound or a pharmaceutical salt, having the following formula:

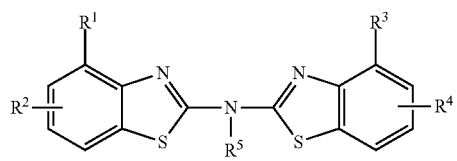

wherein:

$R^1$ is selected from the group consisting of —OH, —CH$_3$, —CH$_2$CH$_3$, —OCH$_3$, —OCH$_2$CH$_3$;

$R^2$ is selected from the group consisting of —H, —OH, —CH$_3$, —CH$_2$CH$_3$, —CH$_2$CH$_2$CH$_3$, —OCH$_3$, —OCH$_2$CH$_2$CH$_3$;

$R^3$ is selected from the group consisting of —F, —Cl, —Br, —I, —CF$_3$;

$R^4$ is selected from the group consisting of —H, —F, —Cl, —Br, —I, —CF$_3$; and $R^5$ is selected from the group consisting of —H, —CH$_3$, —CH$_2$CH$_3$.

2. The compound of claim 1, wherein $R^1$ is —OCH$_3$; $R^2$ is —H or —CH$_3$; $R^3$ is —F, or —CF$_3$; $R^4$ is —H or —F; and $R^5$ is —H.

3. The compound of claim 1, being one of the following compounds:

4-fluoro-N-(4-methoxy benzene (d) thiazole-2-group) benzene (d) thiazole-2-amine;

4,7-difluoro-n-(4-methoxybenzo-thiazole-2-group) benzoylthiazole-2-amine;

4,6-difluoro-n-(4-methoxylbenzene (d) thiazole-2-group) benzene (d) thiazole-2-amine;

4-methoxy-N-(4-(trifluoromethyl) benzo (d) thiazole-2-group) benzo (d) thiazole-2-amine;

N-(4-fluorobenzoyl (d) thiazole-2-group)-4,7-dimethoxy benzozoyl (d) thiazole-2-amine;

N-(4-fluorobenzoyl (d) thiazole-2-group)-4,6-dimethoxy benzozoyl (d) thiazole-2-amine;

4,7-dimethoxyn-(4-(trifluoromethyl) benzene (d) thiazole-2-group) benzene (d) thiazole-2-amine; and 4,6-dimethoxyn-(4-(trifluoromethyl) benzo (d) thiazole-2-group) benzo (d) thiazole-2-amine;

the formulas thereof being as follows, respectively:

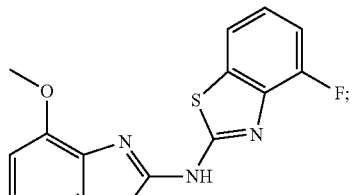

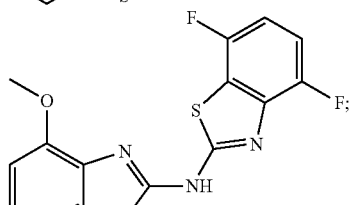

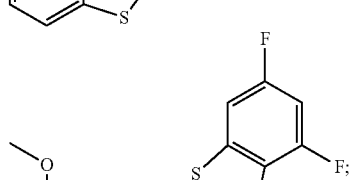

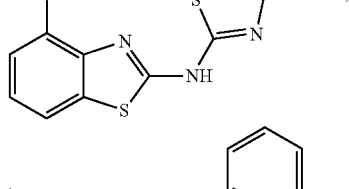

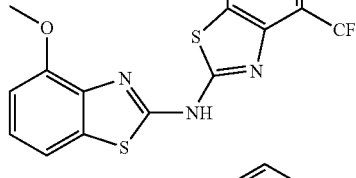

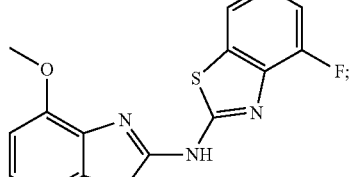

-continued

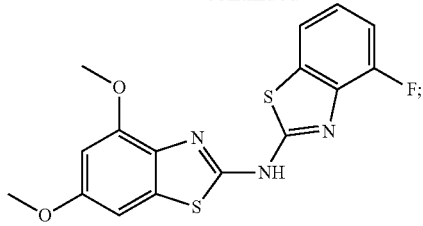

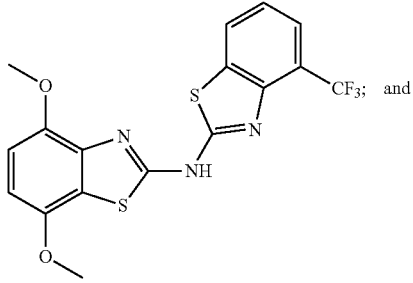

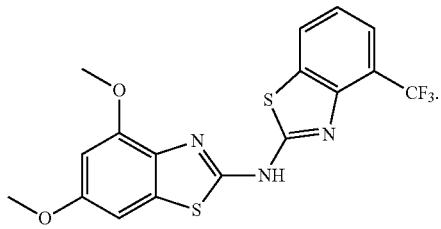

4. A method for preparing the compound of claim 1, the method being implemented according the following flow chart:

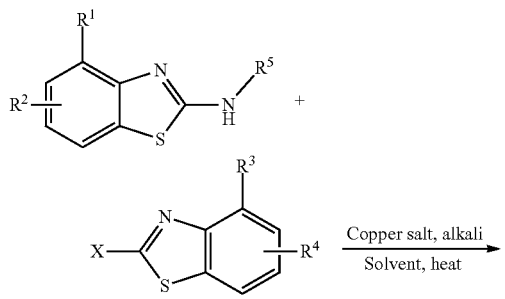

-continued

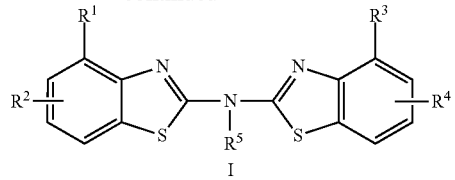

wherein:
X is selected from the group consisting of Cl, Br, and I;
the copper salt is selected from the group consisting of copper oxide, cuprous oxide, copper chloride, cuprous chloride, copper bromide, cuprous bromide and cuprous iodide;
the alkali is selected from the group consisting of sodium hydroxide, potassium hydroxide, potassium carbonate, sodium carbonate, potassium tert-butoxide and sodium hydride;
the solvent is selected from the group consisting of tetrahydrofuran, dimethyl sulfoxide and N,N-dimethylformamide; and
a heating temperature is 80-120° C.

5. The method of claim 4, wherein X is Cl; the copper salt is cuprous iodide; the alkali is potassium carbonate; the solvent is dimethyl sulfoxide; and the heating temperature is 100° C.

6. A pharmaceutical salt of the compound of claim 1.

7. The salt of claim 6, being a product formed by contacting the compound with an acid selected from the group consisting of hydrochloric acid, sulfuric acid, benzenesulfonic acid, p-toluenesulfonic acid, phosphoric acid, hydrobromic acid, maleic acid, fumaric acid and malic acid.

8. A pharmaceutical composition comprising the compound of claim 1.

9. A pharmaceutical composition comprising the pharmaceutical salt of claim 6.

10. A method of preparing a JWA gene activator or an antitumor drug, the method comprising utilizing the compound of claim 1 or a pharmaceutical composition comprising the compound of claim 1.

11. The method of claim 10, wherein the JWA gene activator to activate JWA gene and repress human epidermal growth factor receptor 2 (HER2) of a tumor cell of breast cancer, gastric cancer, lung cancer, and glioma.

\* \* \* \* \*